(12) United States Patent
Adler et al.

(10) Patent No.: US 8,592,223 B2
(45) Date of Patent: Nov. 26, 2013

(54) USE OF PERIOSTIN AS A NOVEL BIOMARKER

(75) Inventors: Sharon Adler, Los Angeles, CA (US); Bancha Satirapoj, Torrance, CA (US); Ying Wang, Torrance, CA (US); Janine LaPage, Redondo Beach, CA (US); Cynthia C. Nast, Rancho Palos Verdes, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 0 days.

(21) Appl. No.: 13/571,211

(22) Filed: Aug. 9, 2012

(65) Prior Publication Data

US 2012/0329886 A1    Dec. 27, 2012

Related U.S. Application Data

(62) Division of application No. 12/924,608, filed on Sep. 29, 2010, now abandoned.

(60) Provisional application No. 61/251,248, filed on Oct. 13, 2009.

(51) Int. Cl.
*G01N 33/566* (2006.01)

(52) U.S. Cl.
CPC ................................. *G01N 33/566* (2013.01)
USPC ............ 436/501; 435/7.1; 435/7.95; 436/518

(58) Field of Classification Search
None
See application file for complete search history.

(56) References Cited

U.S. PATENT DOCUMENTS

| | | | |
|---|---|---|---|
| 2005/0266437 A1* | 12/2005 | Veiby | 435/6 |
| 2010/0221752 A2* | 9/2010 | Gold et al. | 435/7.21 |
| 2011/0067123 A1* | 3/2011 | Andersen et al. | 800/9 |
| 2012/0295361 A1* | 11/2012 | Cerda et al. | 436/71 |

OTHER PUBLICATIONS

Docherty et al., Endoglin regulates renal ischaemia-reperfusion injury, Nephrol Dial Transplant 2006, 21: pp. 2106-2119.*
U.S. Appl. No. 13/665,283, filed Oct. 31, 2012, Adler et al.
US Office Action dated Jan. 27, 2012 issued in U.S. Appl. No. 12/924,608.
Castronovo et al. (2006) "A chemical proteonomics approach for the identification of accessible antigens expressed in human kidney cancer" *Molecular & Cellular Proteomics* 2083-2091.
Coutu et al. (2008) "Periostin, a member of a novel family of vitamin K-dependent proteins, is expressed by mesenchymal stromal cells." *J Biol Chem* 283: 17991-18001.
Dai et al. (2006) "Glucose and diabetes: effects on podocyte and glomerular p38MAPK, heat shock protein 25, and actin cytoskeleton." *Kidney Int* 69: 806-814.
Dai et al. (2009) "Heat shock protein 27 overexpression mitigates cytokine-induced islet apoptosis and streptozotocin-induced diabetes." *Endocrinology* 150: 3031-3039.
Gillan et al. (2002) "Periostin secreted by epithelial ovarian carcinoma is a ligand for alpha(V)beta(3) and alpha(V)beta(5) integrins and promotes cell motility." *Cancer Res* 62: 5358-5364.
Horiuchi et al. (1999) "Identification and characterization of a novel protein, periostin, with restricted expression to periosteum and periodontal ligament and increased expression by transforming growth factor beta." *J Bone Miner Res* 14: 1239-1249.
Humphreys et al. (2010) "Fate tracing reveals the pericyte and not epithelial origin of myofibroblasts in kidney fibrosis." *Am J Pathol* 176: 85-97.
Ito et al. (2002) "Tornado extraction: a method to enrich and purify RNA from the nephrogenic zone of the neonatal rat kidney." *Kidney Int* 62: 763-769.
Iwano et al. (2002) "Evidence that fibroblasts derive from epithelium during tissue fibrosis." *J Clin Invest* 110: 341-350.
Kawashima et al. (2001) "Imaging of Renal Trauma: A Comprehensive Review" *RadioGraphics* 21: 557-574.
Katsuragi et al. (2004) "Periostin as a novel factor responsible for ventricular dilation." *Circulation* 110: 1806-1813.
Kruzynska-Frejtag et al. (2004) "Periostin is expressed within the developing teeth at the sites of epithelial-mesenchymal interaction." *Dev Dyn* 229: 857-868.
LeBaron et al. (1995) "Beta IG-H3, a novel secretory protein inducible by transforming growth factor-beta, is present in normal skin and promotes the adhesion and spreading of dermal fibroblasts in vitro." *J Invest Dermatol.* 104(5): 844-9.
Levey et al. (2007) "Chronic kidney disease as a global public health problem: approaches and initiatives—a position statement from Kidney Disease Improving Global Outcomes." *Kidney Int* 72: 247-259.
Li et al. (2006) "Phosphatidylinositol-3-kinase signaling mediates vascular smooth muscle cell expression of periostin in vivo and in vitro." *Atherosclerosis* 188: 292-300.
Lindner et al. (2005) "Vascular injury induces expression of periostin: implications for vascular cell differentiation and migration." *Arterioscler Thromb Vasc Biol* 25: 77-83.
Litvin et al. (2006) "Periostin and periostin-like factor in the human heart: possible therapeutic targets." *Cardiovasc Pathol* 15: 24-32.
Norris et al. (2004) "Identification and detection of the periostin gene in cardiac development." *Anat Rec a Discov Mol Cell Evol Biol* 281: 1227-1233.
Oku et al. (2008) "Periostin and bone marrow fibrosis." *Int J Hematol* 88: 57-63.
Rani et al. (2009) "Periostin-like-factor and Periostin in an animal model of work-related musculoskeletal disorder." *Bone* 44: 502-512.
Ruan et al. (2009) "The multifaceted role of periostin in tumorigenesis." *Cell Mol Life Sci* 66: 2219-2230.

(Continued)

*Primary Examiner* — Gary W Counts
(74) *Attorney, Agent, or Firm* — Emily M. Haliday; Weaver Austin Villeneuve & Sampson LLP

(57) ABSTRACT

The invention provides, in certain embodiments, a method of assaying an indicator of, and treating, renal injury or renal disease. The method entails assaying a urine sample for periostin, wherein the presence of periostin at an elevated level indicates the presence and/or degree of renal injury or renal disease. The method also involves prescribing, initiating, or altering prophylaxis or therapy for renal injury or renal disease. Also provided, are methods of determining progression of these conditions, as well as methods of determining subjects' response to treatment.

28 Claims, 19 Drawing Sheets
(9 of 19 Drawing Sheet(s) Filed in Color)

(56) References Cited

OTHER PUBLICATIONS

Sasaki et al. (2002) "Expression of the periostin mRNA level in neuroblastoma." *J Pediatr Surg* 37: 1293-1297.

Satirapoj (2009) "Identification of periostin as a novel tissue and urinary biomarker for progressive renal injury" *ASN Renal Week 2009* Abstract 554369 pp. 1-2.

Satirapoj (2009) "Overexpression of Oxidized Low-Density Lipoprotein (Ox-LDL) in the Remnant Kidney after 5/6 Nephrectomy (5/6Nx) and Antigen Transport to Renal Lymph Nodes (RLN)" *ASN Renal Week 2009* Abstract 551732 pp. 1-2.

Sen et al. (2010) "Identification of Periostin as a Novel Matricellular Protein Linked to Progression of Glomerulonephropathies" *ASN Renal Week 2010* Abstract SA-PO2880 p. 1.

Sturm et al. (1975) "Renal Artery and vein injury following blunt trauma" *Ann. Sur.* 186(6): 696-698.

Takayama et al. (2006) "Periostin: a novel component of subepithelial fibrosis of bronchial asthma downstream of IL-4 and IL-13 signals." *J Allergy Clin Immunol* 118: 98-104.

Takeshita et al. (1993) "Osteoblast-specific factor 2: cloning of a putative bone adhesion protein with homology with the insect protein fasciclin I." *Biochem J* 294 ( Pt 1): 271-278.

Vassalotti et al. (2007) "Testing for chronic kidney disease: a position statement from the National Kidney Foundation." *Am J Kidney Dis* 50: 169-180.

Wallace et al. (2008) "Periostin induces proliferation of human autosomal dominant polycystic kidney cells through alphaV-integrin receptor." *Am J Physiol Renal Physiol* 295: F1463-1471.

Yan et al. (2006) "Transduction of a mesenchyme-specific gene periostin into 293T cells induces cell invasive activity through epithelial-mesenchymal transformation." *J Biol Chem* 281: 19700-19708.

U.S. Appl. No. 13/829,163, filed Mar. 14, 2013, Adler et al.

\* cited by examiner

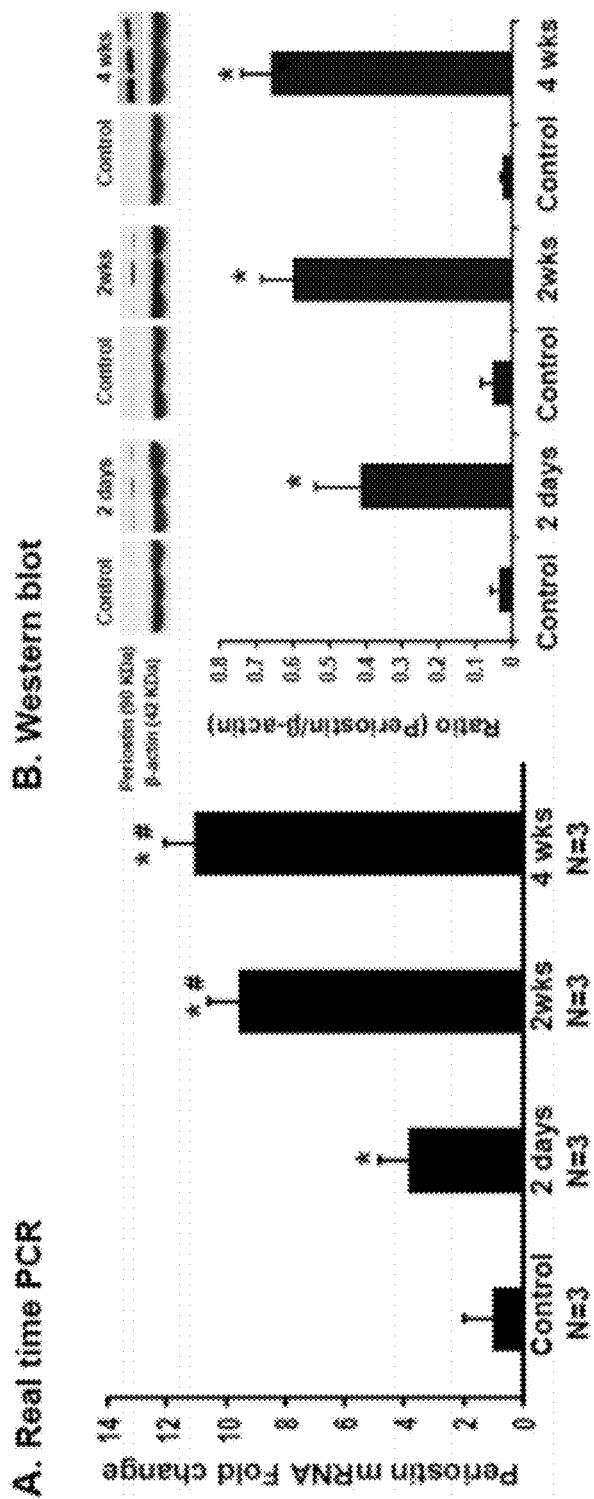
Fig. 1A-B

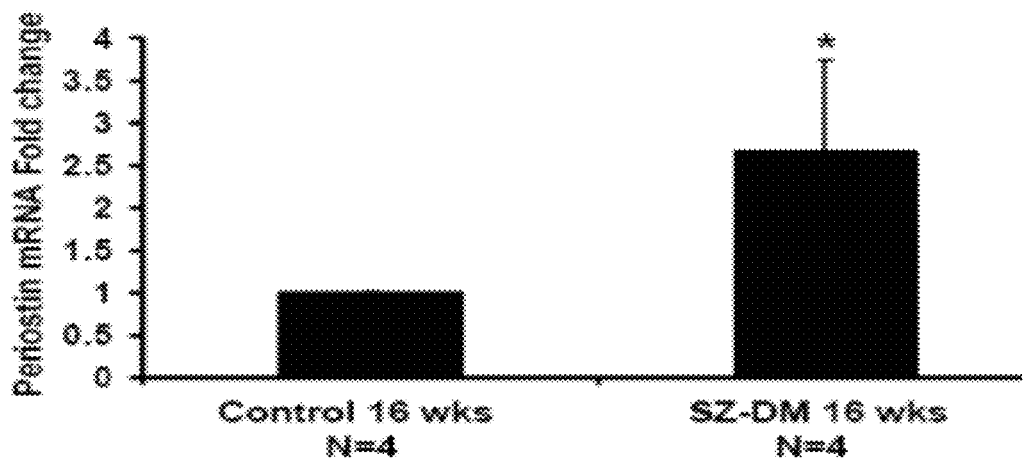
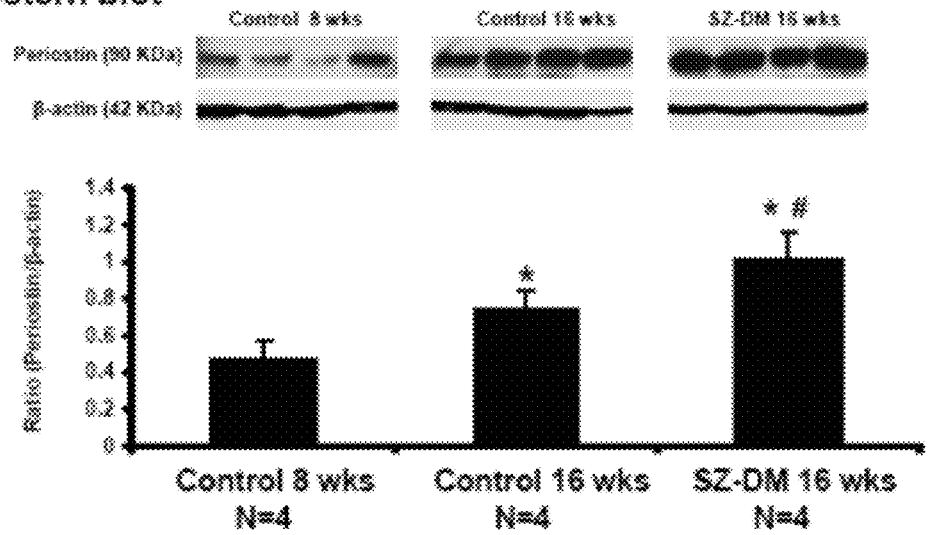
Fig. 2A-B

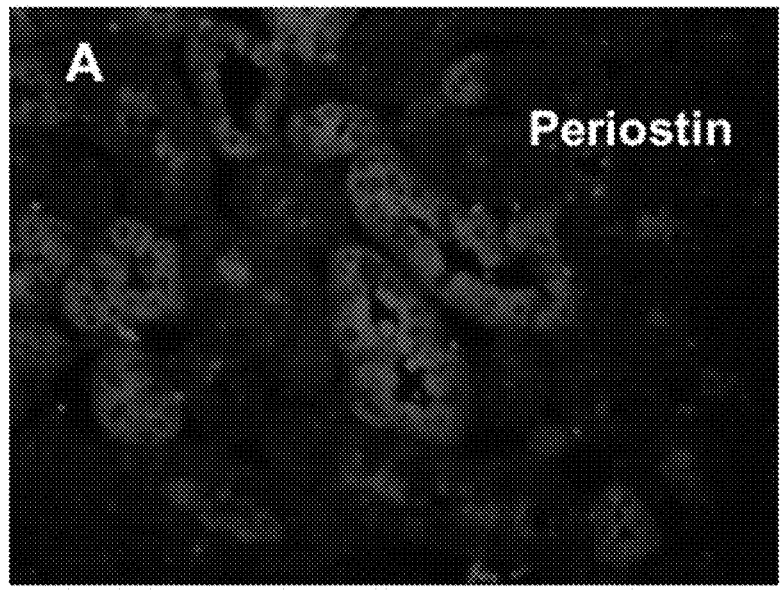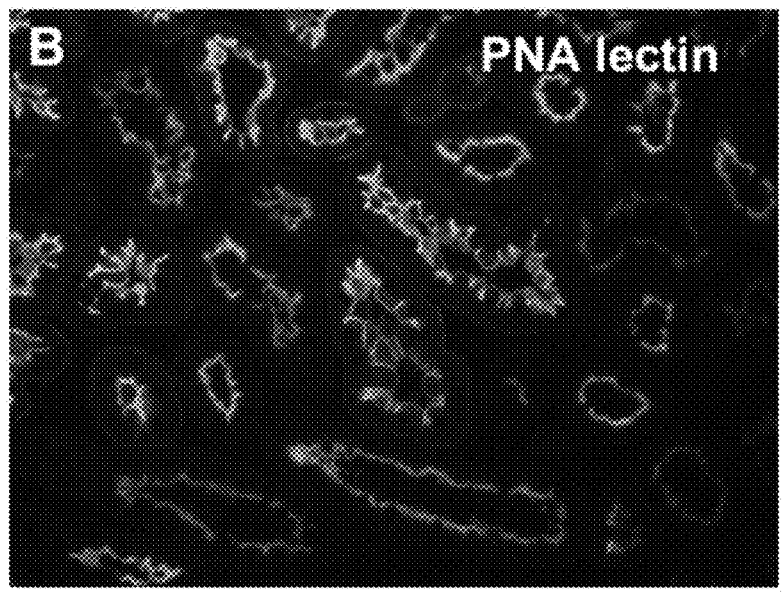
Fig. 3A-B

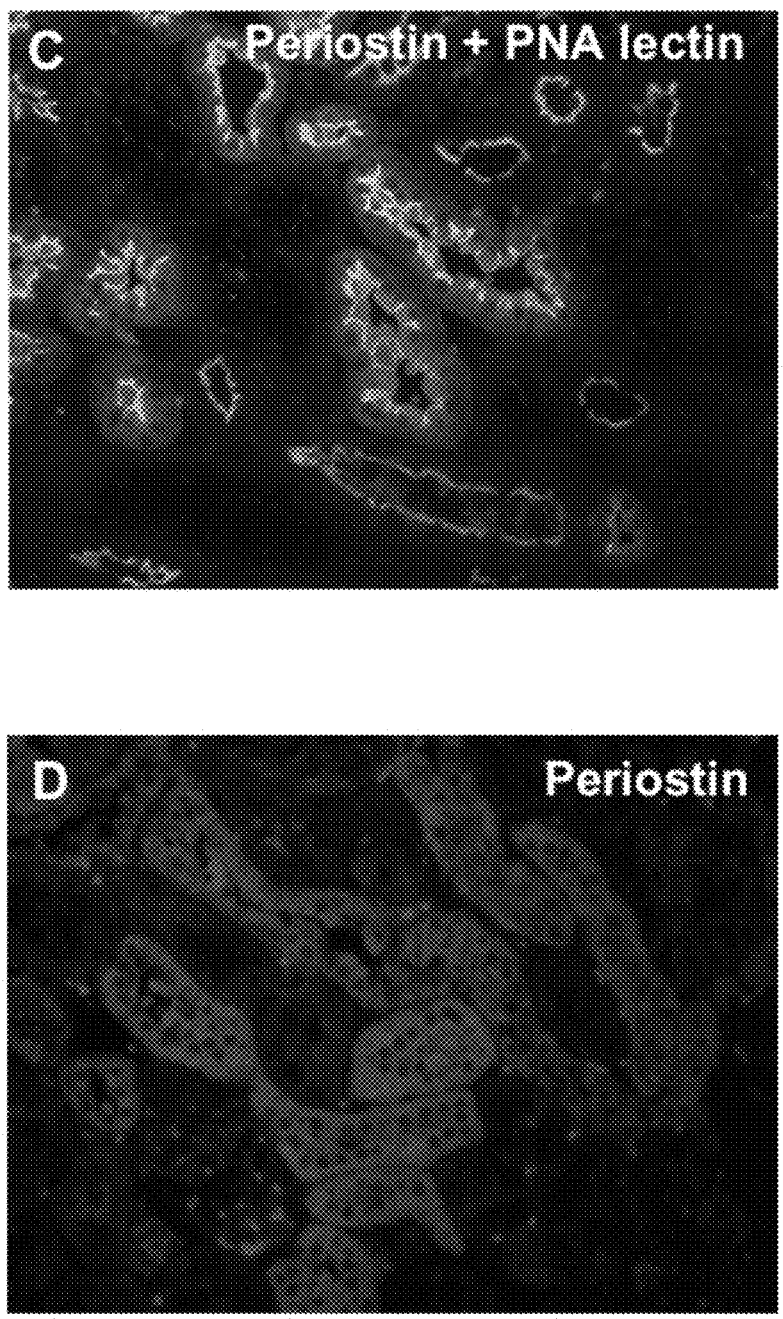
Fig. 3C-D

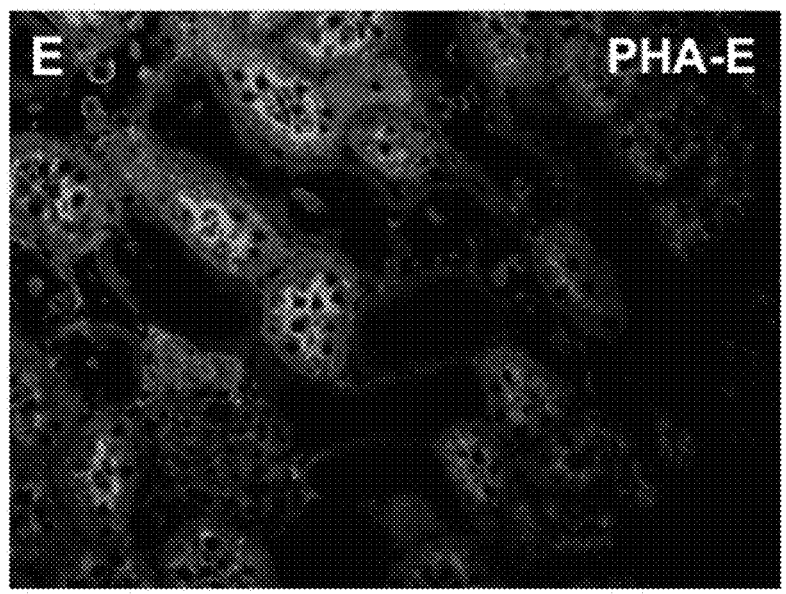
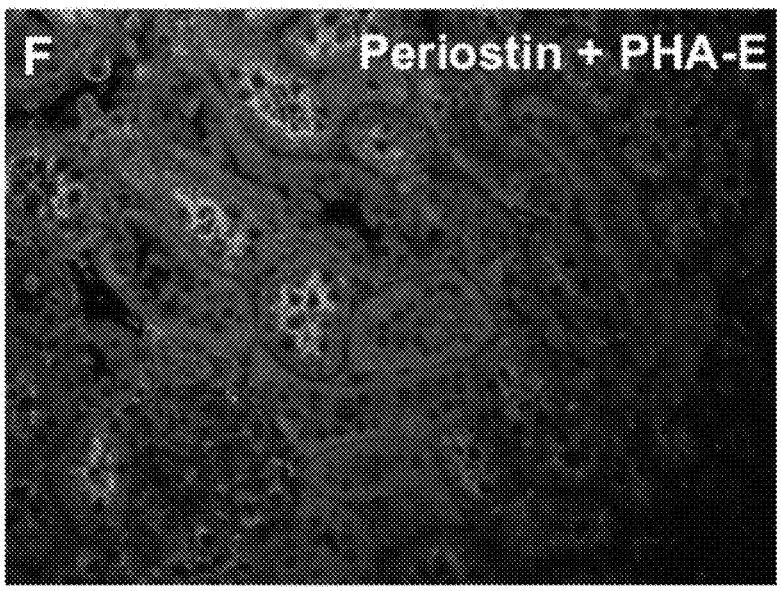
Fig. 3E-F

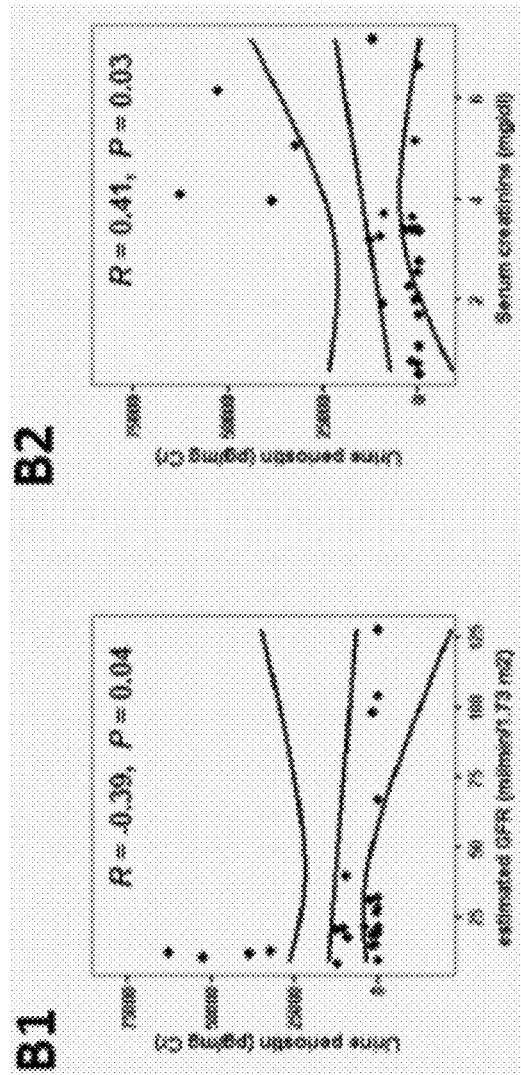
Fig. 7 B1-B2

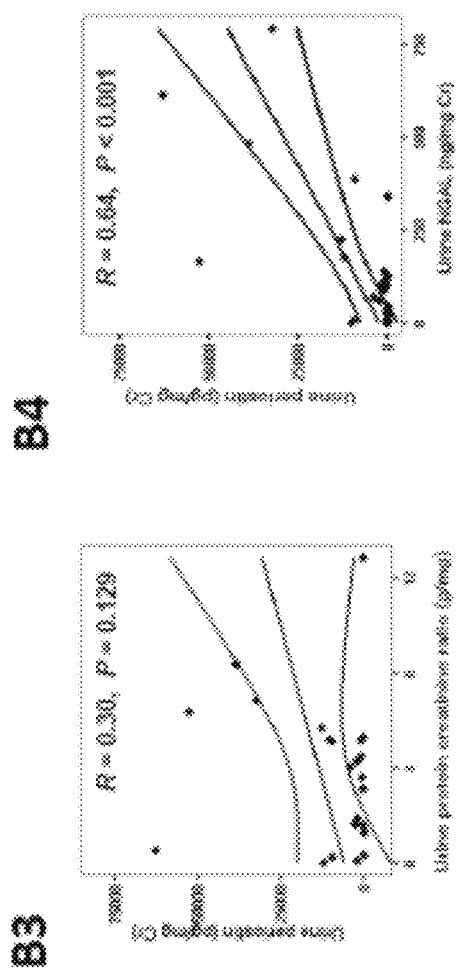
Fig. 7 B3-B4

A
B
Urine periostin in LN patient
with serum creatinine 1.0 mg/dL
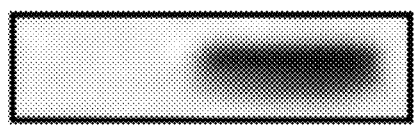
90 kDa
Control   LN patient
*Fig. 8A-B*

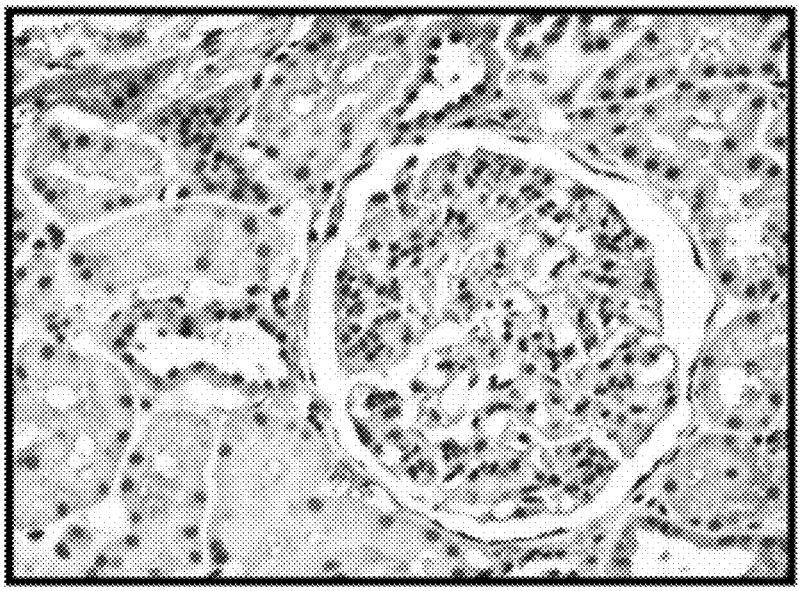
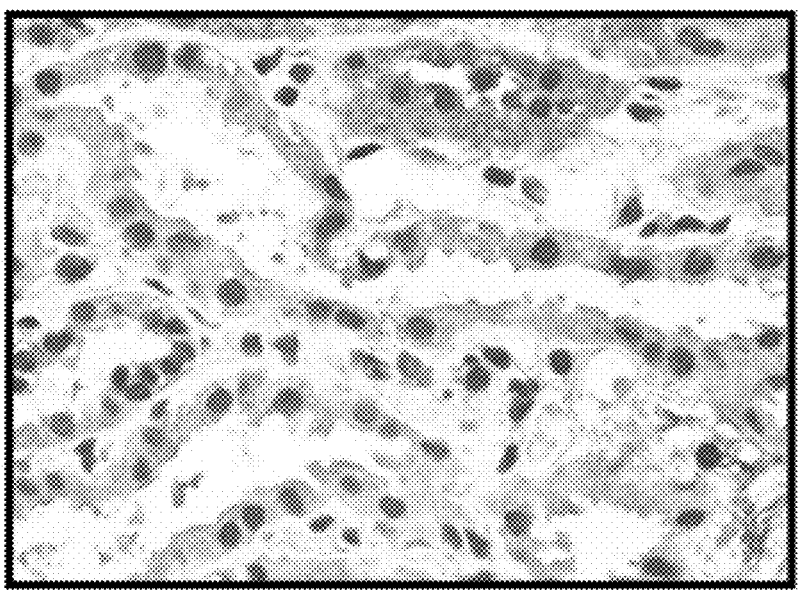
Fig. 8C-D

USE OF PERIOSTIN AS A NOVEL BIOMARKER

CROSS-REFERENCE TO RELATED APPLICATIONS

This application is a divisional of U.S. application Ser. No. 12/924,608, filed Sep. 29, 2010, now abandoned, which claims the benefit of U.S. provisional application No. 61/251,248, filed Oct. 13, 2009, both of which are hereby incorporated by reference in their entireties.

FIELD OF THE INVENTION

The invention relates to the use of periostin as a marker for kidney injury and/or kidney disease.

BACKGROUND OF THE INVENTION

Chronic kidney disease (CKD) is increasing worldwide and is emerging as a major global health threat.[1] Accurately assessing and monitoring renal function is of critical importance in patients with CKD. Currently, kidney injury is clinically tested by serum creatinine, serum cystatin-C, or urine protein or albumin. These are markers that measure kidney functional loss, but not kidney cellular injury. A few urine proteins are also measured as markers of tubulointerstitial injury, but they are either not generally used clinically (e.g., N-acetyl-beta-D-glucosaminidase) or are experimental tests (NGAL, KIM1, Interleukin-18 (IL-18)).

Periostin was initially identified in osteoblasts and acts as an adhesion molecule during bone formation, supports osteoblastic cell line attachment, and is involved in cell survival, proliferation, migration, and differentiation.[3-6] It is induced in processes and pathologies including cardiac embryogenesis, adult cardiac disease, metastatic disease, and tumor suppression.[7] Evidence in these tissues suggests that periostin may play a fundamental role in tissue remodeling [8,9], and in disease of the cardiovascular system.[10-12] Periostin is induced in the kidney during nephrogenesis, but it is not observed in adult kidney under normal conditions.[13] It also may accelerate cyst growth and promote interstitial remodeling in polycystic kidney disease (PKD).[14]

SUMMARY OF THE INVENTION

In certain embodiments, the invention provides a method of detecting an indicator of renal injury or renal disease. The method entails assaying a urine sample for periostin, wherein the presence of periostin at an elevated level indicates the presence and/or degree of renal injury or renal disease. In various embodiments, periostin is detected as a diagnostic indicator of renal injury or renal disease; an indicator of progression, remission, or relapse of renal injury or renal disease; or an indicator of response to treatment for renal injury or renal disease. In specific embodiments, periostin is detected as an indicator of epithelial mesenchymal transition (EMT).

In illustrative embodiments, the urine sample comprises a human urine sample. The urine sample can be, for example, centrifuged urine or urinary exosomes. The human can be, e.g., a human patient known to have, or suspected of having, renal injury or renal disease. The renal disease can be acute or chronic.

In particular embodiments, the invention provides a method of detecting an indicator of a subject's response to treatment for renal injury or renal disease. The method entails assaying a urine sample obtained from a subject after initiation of treatment for renal injury or renal disease for periostin, wherein the level of periostin is positively correlated with the degree of renal injury or renal disease. In certain embodiments, a baseline level of periostin is measured prior to initiation of treatment for renal injury or renal disease. In a variation of such embodiments, the periostin level of the urine sample after initiation of treatment is compared to the baseline level of periostin. A decrease in the periostin level of the urine sample after initiation of treatment, as compared to the baseline level of periostin, indicates that the subject is responding to the treatment. The method can also entail, in some embodiments, performing one or more additional assays of periostin.

Any of the methods described herein can additionally entail detecting one or more additional indicators of renal injury or disease selected from the group consisting of serum creatinine, serum cystatin-C, urine protein, urine albumin, urine N-acetyl-beta-D-glucosaminidase, urine NGAL, IL-18, urine KIM1, and hematopoietic growth factor inducible neurokinin-1 (HGFIN).

In any of these methods, the periostin can be detected by any suitable method, such as, e.g., an immunoassay, HPLC, and mass spectroscopy. The periostin can, for example, be detected in an assay wherein the periostin becomes labeled with a detectable label. In some embodiments, periostin is detected in an assay wherein the periostin is transformed from a free state to a bound state by forming a complex with another assay component. In illustrative embodiments, periostin is detected in an assay wherein periostin initially present in a soluble phase becomes immobilized on a solid phase. The assay can, in some embodiments, entail fractionating the sample to separate periostin from at least one other sample component. In illustrative embodiments, periostin is detected in an assay wherein periostin becomes embedded in a separation medium. In further illustrative embodiments, periostin is detected in an assay wherein periostin is volatilized.

Any of the methods described herein can additionally entail recording the periostin level, and/or a diagnosis based at least in part on the periostin level, in a patient medical record. This recordation can include recording the periostin level in a computer-readable medium. In various embodiments, the patient medical record is maintained by a laboratory, physician's office, a hospital, a health maintenance organization, an insurance company, or a personal medical record website. In certain embodiments, a diagnosis, based at least in part on the periostin level, is recorded on or in a medic alert article, such as a card, worn article, or radiofrequency identification (RFID) tag.

Any of the methods described herein can additionally entail informing the subject of a result of the periostin assay and/or of a diagnosis based at least in part on the periostin level. These methods can also entail prescribing, initiating, and/or altering prophylaxis and/or therapy. In particular embodiments, the methods entail ordering and/or performing one or more additional assays. For example, if the periostin level determined in an initial periostin assay is not elevated, and the additional assay comprises an additional periostin assay (e.g., at a later date). If the periostin level determined in an initial periostin assay is elevated, an additional periostin assay can be carried out (for confirmation of the elevated level) or a different assay can be carried out, e.g., to detect a different biomarker of renal injury or disease.

In any of the methods described here, periostin is detected as part of a differential diagnosis of renal injury or disease.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3. Periostin localizes exclusively to tubular cells of the distal nephron after 5/6Nx. Paraffin-embedded sections were double labeled with antibodies against periostin (red, A, D) and either distal nephron marker PNA lectin (green, B) or proximal nephron marker PHA-E lectin (green, E). Periostin co-localized with PNA staining exclusively in the distal nephron (C), but never with PHA-E staining in the proximal nephron (F). Merged images show periostin in red and PNA or PHA-E in green (Original magnification: 200×). Cell nuclei were stained with DAPI (C and F).

FIG. 8. Urine periostin is measurable before a rise in serum creatinine is discernible in renal tissue from a patient with LN in which tubular atrophy is present. (A) Renal biopsy showing proliferative lupus glomerulonephritis with an area of established tubular atrophy (arrow) (Jones stain, Original magnification: ×200). (B) Immunoblotting demonstrating 90 kDa urine periostin in lightly centrifuged urine, but none in control. (C) Periostin immunostaining (brown; H&E counterstain, Original magnification: ×200) shows cytoplasmic tubular cell expression including expression in sloughed luminal cell fragment (arrow). (D) Tubular cells with heavy diffuse cytoplasmic periostin immunostaining (arrow) (Original magnification: ×400).

DETAILED DESCRIPTION

Definitions

Figure 1C:
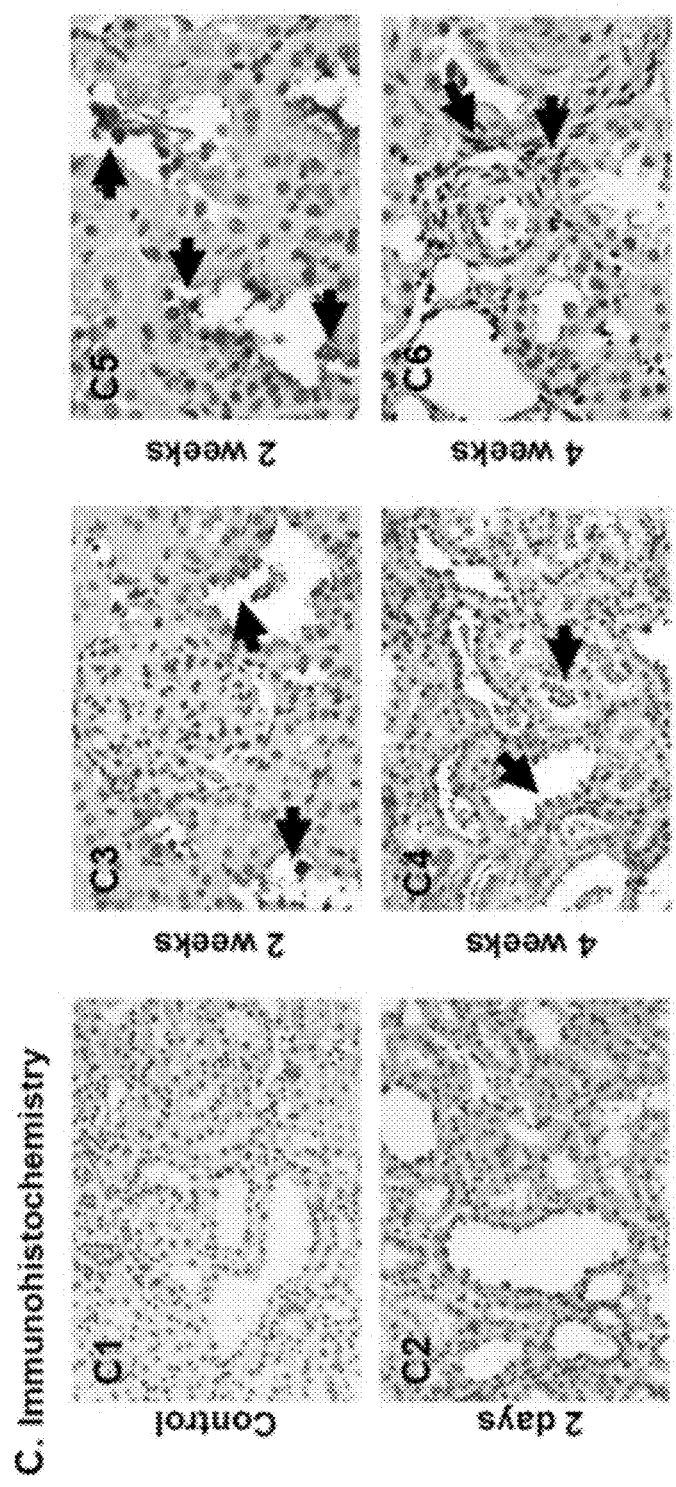
FIG. 1. Renal periostin increases after 5/6Nx in rats. (A) Periostin mRNA expression increased over time after 5/6Nx in RK compared to control kidney tissue in samples in which the infarct tissue was excised. The expression of 18 S was used as an internal control. (B) Immunoblotting analysis for periostin was also increased in RK compared to control kidneys. (C) Periostin immunostaining was not detected in cortical control rat kidney (C1). In contrast, representative sections of kidney tissues at 2 days, 2 weeks, and 4 weeks displayed cytoplasmic staining for periostin, most prominently in the apical portion of tubular cells, with stronger and more diffuse tubular cell staining at 2 and 4 weeks. There also was periostin staining in casts and/or in sloughed cells in the tubular lumina (C3, C4, arrows). There was no glomerular staining for periostin (C3) (C1-4 Original magnification: 400×). (C5) Renal tubules demonstrated apical periostin in the 2 week RK. Tubules contained luminal sloughed cells and cellular debris which stained strongly for periostin (arrows) (Original magnification: 600×). (C6) 4 week RK had periostin positive interstitial cells (arrows) which frequently were in the periadventitial area around arteries and arterioles. (Original magnification: 400×). * $P<0.05$ vs. control group, #$P<0.05$ vs. 2 days after 5/6Nx group.

Terms used in the claims and specification are defined as set forth below unless otherwise specified.

"Biological samples" that can be assayed using the methods of the present invention include biological fluids, such as kidney tissue and cells, whole blood, blood leukocytes, serum, and urine.

As used herein with reference to periostin, the term "elevated level" refers to a level in a biological sample that is higher than a normal level or range. The normal level or range for periostin is defined in accordance with standard practice. Thus, the level measured in a particular biological sample will be compared with the level or range of levels determined in similar normal samples. In this context, "normal tissue" is tissue from an individual with no detectable renal disease and/or renal injury. The level of periostin is said to be "elevated" where the periostin is normally undetectable (i.e, the normal level in the tissue is zero), but is detected in a test sample, as well as where the periostin is present in the test sample at a higher than normal level or range.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain (VL)" and "variable heavy chain (VH)" refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. Huston, et al. (1988) Proc. Nat. Acad. Sci. USA, 85: 5879-5883. While the VH and VL are connected to each as a single polypeptide chain, the VH and VL domains associate non-covalently. The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778).

The term "specific binding" is defined herein as the preferential binding of binding partners to another (e.g., two polypeptides, a polypeptide and nucleic acid molecule, or two nucleic acid molecules) at specific sites. The term "specifically binds" indicates that the binding preference (e.g., affinity) for the target molecule/sequence is at least 2-fold, more preferably at least 5-fold, and most preferably at least 10- or 20-fold over a non-specific target molecule (e.g. a randomly generated molecule lacking the specifically recognized site(s)).

As used herein, the phrase "periostin becomes labeled with a detectable label" refers to the binding of a label or labeled moiety to periostin, directly or indirectly, via one or more additional moieties.

As used with reference to periostin, a "free state" refers to the state of periostin before contact with any assay component. This term encompasses periostin bound to one or more sample components. The term "bound state" is used to describe periostin bound to one or more assay component(s) to form a complex.

The term "medical record" or "patient medical record" refers to an account of a patient's examination and/or treatment that typically includes one or more of the following: the patient's medical history and complaints, the physician's physical findings, the results of diagnostic tests and procedures, and patient medications and therapeutic procedures. A medical record is typically made by one or more physicians and/or physicians' assistants and is a written, transcribed or otherwise recorded record and/or history of various illnesses or injuries requiring medical care, and/or inoculations, and/or allergies, and/or treatments, and/or prognosis, and/or frequently health information about parents, siblings, and/or occupation. The record may be reviewed by a physician in diagnosing the condition.

As used herein, the term "worn article" refers to any article that can be worn on a subject's body, including, but not limited to, a tag, bracelet, necklace, arm band, or head band.

As used herein, the term "differential diagnosis" refers to the determination of which of two or more diseases with similar symptoms is likely responsible for a subject's symptom(s), based on an analysis of the clinical data.

In General

Early recognition is important to slowing kidney disease progression, maintaining quality of life, and improving outcomes. Accurately assessing and monitoring renal function is of critical importance in patients with kidney disease. Biomarkers for early kidney disease and for kidney disease progression are currently not sensitive or specific. More sensitive and specific biomarkers are needed to diagnose kidney injury at an early stage and to assess response (either injurious of state or remission) to treatments.

In certain embodiments, the invention provides methods of detecting periostin as a novel biomarker of renal injury and/or renal disease. These methods entail assaying a biological sample for periostin, wherein the level of periostin is positively correlated with renal injury and/or renal disease. In various embodiments, these methods are useful in diagnosing acute kidney injury as well as ongoing kidney injury, obviating the need for an initial or one or more serial kidney biopsies in some clinical situations. In other embodiments, these methods can be employed to assess response to therapy and/or identify relapse of kidney injury. Furthermore, these methods are unique in that they have the capability of non-invasively assessing, in a quantitative manner, a particular pathophysiologic process (e.g., epithelial mesnchymal transformation (EMT)) that is a major driver of progressive renal injury. Measurement of periostin, e.g., in urine, provides a surrogate measure of EMT and therefore a valuable tool for assessing the success of treatments for kidney diseases.

Sample Collection and Processing

The assay methods of the invention are generally carried out on biological samples derived from an animal, preferably a mammal, and more preferably a human.

The methods of the invention can be carried out using any sample that may contain soluble periostin, periostin in exosomes, or periostin moieties, including its intracellular, transmembrane, or extracellular moieties or any peptide fraction thereof. Convenient samples include, for example, blood, blood cells, serum, plasma, kidney cells, urinary exosomes, and urine.

The sample may be pretreated as necessary by dilution in an appropriate buffer solution or concentrated, if desired. Any of a number of standard aqueous buffer solutions and/or protease inhibitors, employing any of a variety of buffers, such as phosphate, Tris, or the like, at physiological pH, can be used.

Assaying for Periostin

Periostin can be detected and quantified by any of a number of methods well known to those of skill in the art for polypeptide detection. These may include analytic biochemical methods such as electrophoresis, capillary electrophoresis, high performance liquid chromatography (HPLC), thin layer chromatography (TLC), hyperdiffusion chromatography, mass spectroscopy and the like, or various immunological methods such as fluid or gel precipitin reactions, immunodiffusion (single or double), immunohistochemistry, affinity chromatography, immunoelectrophoresis, radioimmunoassay (RIA), enzyme-linked immunosorbent assays (ELISAs), immunofluorescent assays, Western blotting, and the like.

In one embodiment, periostin is detected/quantified in an electrophoretic polypeptide separation (e.g. a 1- or 2-dimensional electrophoresis). Means of detecting polypeptides using electrophoretic techniques are well known to those of skill in the art (see generally, R. Scopes (1982) Polypeptide Purification, Springer-Verlag, N.Y.; Deutscher, (1990) Methods in Enzymology Vol. 182: Guide to Polypeptide Purification, Academic Press, Inc., N.Y.).

A variation of this embodiment utilizes a Western blot (immunoblot) analysis to detect and quantify the presence of periostin in the sample. This technique generally comprises separating sample polypeptides by gel electrophoresis on the basis of molecular weight, transferring the separated polypeptides to a suitable solid support (such as a nitrocellulose filter, a nylon filter, or derivatized nylon filter), and incubating the sample with antibodies that specifically bind the analyte. Antibodies that specifically bind to the analyte may be directly labeled or alternatively may be detected subsequently using labeled antibodies (e.g., labeled sheep anti-mouse antibodies) that specifically bind to a domain of the primary antibody.

In certain of the above-described embodiments, the sample and/or periostin is transformed in some manner in the course of the assay. For example, the sample may be fractionated such that periostin is separated from at least one other sample component. The periostin can be recovered in a liquid fraction or can be detected while embedded in a separation medium, such as a gel. For mass spectroscopy, periostin is volatilized for detection.

In a preferred embodiment, periostin is detected and/or quantified in the biological sample using any of a number of well-known immunoassays (see, e.g., U.S. Pat. Nos. 4,366, 241; 4,376,110; 4,517,288; and 4,837,168). For a general review of immunoassays, see also Methods in Cell Biology Volume 37: Antibodies in Cell Biology, Asai, ed. Academic Press, Inc. New York (1993); Basic and Clinical Immunology 7th Edition, Stites & Terr, eds. (1991).

Conventional immunoassays often utilize a "capture agent" to specifically bind to and often immobilize the analyte on a solid phase. In preferred embodiments, the capture agent is an antibody.

Immunoassays also typically utilize a labeled detection agent to specifically bind to and label the binding complex formed by the capture agent and the analyte. The labeled detection agent may itself be one of the moieties making up the antibody/analyte complex. Alternatively, the labeled detection agent may be a third moiety, such as another antibody, that specifically binds to the capture agent/analyte complex. Other polypeptides capable of specifically binding immunoglobulin constant regions, such as polypeptide A or polypeptide G may also make up the labeled detection agent. These polypeptides are normal constituents of the cell walls of streptococcal bacteria. They exhibit a strong non-immunogenic reactivity with immunoglobulin constant regions from a variety of species (see, generally Kronval, et al. (1973) J. Immunol., 111: 1401-1406, and Akerstrom (1985) J. Immunol., 135: 2589-2542).

Preferred immunoassays for detecting the target polypeptide(s) are either competitive or noncompetitive. Noncompetitive immunoassays are assays in which the amount of captured analyte is directly measured. In competitive assays, the amount of analyte in the sample is measured indirectly by measuring the amount of an added (exogenous) labeled analyte displaced (or competed away) from a capture agent by the analyte present in the sample. In one competitive assay, a known amount of, in this case, labeled periostin is added to the sample, and the sample is then contacted with a capture agent. The amount of labeled periostin bound to the antibody is inversely proportional to the concentration of periostin present in the sample.

In illustrative embodiments, periostin is measured in urine using a "dipstick" assay.

The assays of this invention are scored (as positive or negative or quantity of analyte) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of analyte concentration.

Antibodies

Antibodies useful in the immunoassay methods of the invention include polyclonal and monoclonal antibodies. Polyclonal antibodies are raised by injecting (e.g., subcutaneous or intramuscular injection) an immunogen into a suitable non-human mammal (e.g., a mouse or a rabbit). Generally, the immunogen should induce production of high titers of antibody with relatively high affinity for the target antigen.

If desired, the antigen may be conjugated to a carrier protein by conjugation techniques that are well known in the art. Commonly used carriers include keyhole limpet hemocyanin (KLH), thyroglobulin, bovine serum albumin (BSA), and tetanus toxoid. The conjugate is then used to immunize the animal.

The antibodies are then obtained from blood samples taken from the animal. The techniques used to produce polyclonal antibodies are extensively described in the literature (see, e.g., Methods of Enzymology, "Production of Antisera With Small Doses of Immunogen: Multiple Intradermal Injections," Langone, et al. eds. (Acad. Press, 1981)). Polyclonal antibodies produced by the animals can be further purified, for example, by binding to and elution from a matrix to which the target antigen is bound. Those of skill in the art will know of various techniques common in the immunology arts for purification and/or concentration of polyclonal, as well as monoclonal, antibodies see, for example, Coligan, et al. (1991) Unit 9, Current Protocols in Immunology, Wiley Interscience.

For many applications, monoclonal antibodies (mAbs) are preferred. The general method used for production of hybridomas secreting mAbs is well known (Kohler and Milstein (1975) Nature, 256:495). Briefly, as described by Kohler and Milstein, the technique entailed isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody that bound to cancer cell lines. Confirmation of specificity among mAbs can be accomplished using routine screening techniques (such as the enzyme-linked immunosorbent assay, or "ELISA") to determine the elementary reaction pattern of the mAb of interest.

As used herein, the term "antibody" encompasses antigen-binding antibody fragments, e.g., single chain antibodies (scFv or others), which can be produced/selected using phage display technology. The ability to express antibody fragments on the surface of viruses that infect bacteria (bacteriophage or phage) makes it possible to isolate a single binding antibody fragment, e.g., from a library of greater than $10^{10}$ nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) Nature, 348: 552-554; Hoogenboom et al. (1991) Nucleic Acids Res. 19: 4133-4137).

Since the antibody fragments on the surface of the phage are functional, phage-bearing antigen-binding antibody fragments can be separated from non-binding phage by antigen affinity chromatography (McCafferty et al. (1990) Nature, 348: 552-554). Depending on the affinity of the antibody fragment, enrichment factors of 20-fold-1,000,000-fold are obtained for a single round of affinity selection. By infecting bacteria with the eluted phage, however, more phage can be grown and subjected to another round of selection. In this way, an enrichment of 1000-fold in one round can become 1,000,000-fold in two rounds of selection (McCafferty et al. (1990) Nature, 348: 552-554). Thus, even when enrichments are low (Marks et al. (1991) J. Mol. Biol. 222: 581-597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) J. Mol. Biol. 222: 581-597). In one embodiment, natural VH and VL repertoires present in human peripheral blood lymphocytes are isolated from unimmunized donors by PCR. The V-gene repertoires can be spliced together at random using PCR to create a scFv gene repertoire which can be cloned into a phage vector to create a library of 30 million phage antibodies (Id.). From a single "naïve" phage antibody library, binding antibody fragments have been isolated against more than 17 different antigens, including haptens, polysaccharides, and proteins (Marks et al. (1991) J. Mol. Biol. 222: 581-597; Marks et al. (1993). Bio/Technology. 10: 779-783; Griffiths et al. (1993) EMBO J. 12: 725-734; Clackson et al. (1991) Nature. 352: 624-628). Antibodies have been produced against self proteins, including human thyroglobulin, immunoglobulin, tumor necrosis factor, and CEA (Griffiths et al. (1993) EMBO J. 12: 725-734). The antibody fragments are highly specific for the antigen used for selection and have affinities in the 1 nM to 100 nM range (Marks et al. (1991) J. Mol. Biol. 222: 581-597; Griffiths et al. (1993) EMBO J. 12: 725-734). Larger phage antibody libraries result in the isolation of more antibodies of higher binding affinity to a greater proportion of antigens.

As those of skill in the art readily appreciate, antibodies can be prepared by any of a number of commercial services (e.g., Berkeley antibody laboratories, Bethyl Laboratories, Anawa, Eurogenetec, etc.).

Solid Phase

For embodiments of the invention that employ a solid phase as a support for the capture agent, the solid phase can be any suitable porous material with sufficient porosity to allow access by reagents and a suitable surface affinity to bind a capture agent. Microporous structures are generally preferred, but materials with gel structure in the hydrated state may be used as well. Useful solid supports include: natural polymeric carbohydrates and their synthetically modified, crosslinked, or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials);

and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto, bonded, or laminated to appropriate inert carriers, such as paper, glass, plastic films, fabrics, or the like.

The porous structure of nitrocellulose has excellent absorption and adsorption qualities for a wide variety of reagents including monoclonal antibodies. Nylon also possesses similar characteristics and also is suitable.

Porous solid phases useful in the invention can be in the form of sheets of thickness from about 0.01 to 0.5 mm, e.g., about 0.1 mm. The pore size may vary within wide limits, and is preferably from about 0.025 to about 15 microns, especially from about 0.15 to about 15 microns.

Preferred solid phase materials for flow-through assay devices include filter paper such as a porous fiberglass material or other fiber matrix materials. The thickness of such material is not critical and will be a matter of choice, largely based upon the properties of the sample or analyte being assayed, such as the fluidity of the biological sample.

Alternatively, the solid phase can constitute microparticles. Microparticles useful in the invention can be selected by one skilled in the art from any suitable type of particulate material and include those composed of polystyrene, polymethylacrylate, polypropylene, latex, polytetrafluoroethylene, polyacrylonitrile, polycarbonate, or similar materials.

Microparticles can be suspended in the mixture of soluble reagents and biological sample or can be retained and immobilized by a support material. In the latter case, the microparticles on or in the support material are not capable of substantial movement to positions elsewhere within the support material.

The methods of the present invention can be adapted for use in systems that utilize microparticle technology including automated and semi-automated systems wherein the solid phase comprises a microparticle. Such systems include those described in pending U.S. application Ser. No. 425,651 and U.S. Pat. No. 5,089,424, which correspond to published EPO App. Nos. EP 0 425 633 and EP 0 424 634, respectively, and U.S. Pat. No. 5,006,309.

In particular embodiments, the solid phase includes one or more electrodes. Capture agent(s) can be affixed, directly or indirectly, to the electrode(s). In one embodiment, for example, capture agents can be affixed to magnetic or paramagnetic microparticles, which are then positioned in the vicinity of the electrode surface using a magnet. Systems in which one or more electrodes serve as the solid phase are useful where detection is based on electrochemical interactions. Exemplary systems of this type are described, for example, in U.S. Pat. No. 6,887,714 (issued May 3, 2005). The basic method is described further below with respect to electrochemical detection.

The capture agent can be attached to the solid phase by adsorption on the porous material, where it is retained by hydrophobic forces. Alternatively, the surface of the solid phase can be activated by chemical processes that cause covalent linkage of the capture agent to the support.

To change or enhance the intrinsic charge of the solid phase, a charged substance can be coated directly onto the solid phase material or onto microparticles which then are retained by a solid phase material. Ion capture procedures for immobilizing an immobilizable reaction complex with a negatively charged polymer, described in U.S. applicaton Ser. No. 150,278, corresponding to EP Publication No. 0326100, and U.S. application Ser. No. 375,029 (EP Publication No. 0406473), can be employed according to the present invention to affect a fast solution-phase immunochemical reaction. In these procedures, an immobilizable immune complex is separated from the rest of the reaction mixture by ionic interactions between the negatively charged polyanion/immune complex and the previously treated, positively charged porous matrix and detected by using any of a number of signal-generating systems, including, e.g., chemiluminescent systems, as described in U.S. application Ser. No. 921,979, corresponding to EPO Publication No. 0 273,115.

If the solid phase is silicon or glass, the surface must generally be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)-trimethoxy silane (Sigma Chemical Co., St. Louis, Mo.) can be used to introduce reactive groups such as amino-, vinyl, and thiol, respectively. Such activated surfaces can be used to link the capture directly (in the cases of amino or thiol), or the activated surface can be further reacted with linkers such as glutaraldehyde, bis(succinimidyl) suberate, SPPD 9 succinimidyl 3-[2-pyridyldithio]propionate), SMCC (succinimidyl-4-[Nmaleimidomethyl]cyclohexane-1-carboxylate), SIAB (succinimidyl [4iodoacetyl]aminobenzoate), and SMPB (succinimidyl 4-[1maleimidophenyl]butyrate) to separate the capture agent from the surface. Vinyl groups can be oxidized to provide a means for covalent attachment. Vinyl groups can also be used as an anchor for the polymerization of various polymers such as poly-acrylic acid, which can provide multiple attachment points for specific capture agents. Amino groups can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons; available from Sigma Chemical Co., St. Louis, Mo.). Additionally, polyelectrolyte interactions can be used to immobilize a specific capture agent on a solid phase using techniques and chemistries described U.S. application Ser. No. 150,278, filed Jan. 29, 1988, and U.S. application Ser. No. 375,029, filed Jul. 7, 1989, each of which is incorporated herein by reference.

Other considerations affecting the choice of solid phase include the ability to minimize non-specific binding of labeled entities and compatability with the labeling system employed. For, example, solid phases used with fluorescent labels should have sufficiently low background fluorescence to allow signal detection.

Following attachment of a specific capture agent, the surface of the solid support may be further treated with materials such as serum, proteins, or other blocking agents to minimize non-specific binding.

Labeling Systems

As discussed above, many immunoassays according to the invention employ a labeled detection agent.

Detectable labels suitable for use in the detection agents of the present invention include any composition detectable by spectroscopic, photochemical, biochemical, immunochemical, electrical, optical, or chemical means. Useful labels in the present invention include magnetic beads (e.g., Dynabeads™), fluorescent dyes (e.g., fluorescein, texas red, rhodamine, green fluorescent protein, and the like, see, e.g., Molecular Probes, Eugene, Oreg., USA), chemiluminescent compounds such as acridinium (e.g., acridinium-9-carboxamide), phenanthridinium, dioxetanes, luminol and the like, radiolabels (e.g., $^3$H, $^{125}$I, $^{35}$S, $^{14}$C, or $^{32}$P), catalysts such as enzymes (e.g., horse radish peroxidase, alkaline phosphatase, beta-galactosidase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

The label can be attached to the detection agent prior to, or during, or after contact with the biological sample. So-called "direct labels" are detectable labels that are directly attached to or incorporated into detection agents prior to use in the assay. Direct labels can be attached to or incorporated into detection agents by any of a number of means well known to those of skill in the art.

In contrast, so-called "indirect labels" typically bind to the detection agent at some point during the assay. Often, the indirect label binds to a moiety that is attached to or incorporated into the detection agent prior to use. Thus, for example, an antibody used as a detection agent (a "detection antibody") can be biotinylated before use in an assay. During the assay, an avidin-conjugated fluorophore can bind the biotin-bearing detection agent, to provide a label that is easily detected.

In another example of indirect labeling, polypeptides capable of specifically binding immunoglobulin constant regions, such as polypeptide A or polypeptide G, can also be used as labels for detection antibodies. Such polypeptides can thus be labeled and added to the assay mixture, where they will bind to the detection antibody.

Some labels useful in the invention may require the use of an indicator reagent to produce a detectable signal. In an ELISA, for example, an enzyme label (e.g., beta-galactosidase) will require the addition of a substrate (e.g., X-gal) to produce a detectable signal.

Periostin Levels

Once determined, a periostin level can be recorded in a patient medical record. In certain embodiments, the methods of the invention include making a diagnosis, often a differential diagnosis, based at least in part on the periostin level. This diagnosis can also be recorded in a patient medical record. For example, in various embodiments, the diagnosis of renal injury and/or renal disease (acute or chronic) is recorded in a medical record. The medical record can be in paper form and/or can be maintained in a computer-readable medium. The medical record can be maintained by a laboratory, physician's office, a hospital, a health maintenance organization, an insurance company, and/or a personal medical record website. In certain embodiments, a diagnosis, based at least in part on the periostin level, is recorded on or in a medic alert article such as a card, a worn article, and/or a radiofrequency identification (RFID) tag.

In particular embodiments, the methods of the invention include informing the subject of a result of the periostin assay and/or of a diagnosis based at least in part on the periostin level. The patient can be informed verbally, in writing, and/or electronically.

The methods of the invention can include prescribing, initiating, and/or altering prophylaxis and/or therapy, e.g., for renal injury and/or renal disease (acute or chronic). In certain embodiments, the methods can entail ordering and/or performing one or more additional assays. For example, if the periostin level is determined to be within a normal range (i.e., not elevated), the periostin assay may be repeated to rule out a false negative result, and/or one or more additional periostin assays may be performed to monitor the subject's status. If the periostin level is determined to be elevated, it may be desirable repeat the periostin assay to rule out a false positive result. In certain embodiments, it will be desirable to assay another indicator of, e.g., renal injury and/or renal disease (acute or chronic), to confirm a diagnosis. Exemplary indicators of renal injury or disease include serum creatinine, serum cystatin-C, urine protein, urine albumin, urine N-acetyl-beta-D-glucosaminidase, urine NGAL, IL-18, urine KIM1, and hematopoietic growth factor inducible neurokinin-1 (HGFIN). The use of HGFIN as an indicator of renal injury or disease is described in U.S. patent application Ser. No. 12/613,385, filed Nov. 5, 2009, which is hereby incorporated by reference in its entirety and specifically for this description. Urine periostin may be sequentially measured in patients in whom the assay shows kidney injury in order to demonstrate remission, and in those with remission, in order to demonstrate relapse of kidney injury. In the setting of experimental drug testing, urine periostin may be used alone or as a member of a biomarker panel to demonstrate early kidney injury either in preclinical and/or clinical testing.

Test Kits

The invention also provides a test kit for assaying for periostin. Test kits according to the invention include one or more reagents useful for practicing one or more immunoassays according to the invention. A test kit generally includes a package with one or more containers holding the reagents, as one or more separate compositions or, optionally, as admixture where the compatibility of the reagents will allow. The test kit can also include other material(s) that may be desirable from a user standpoint, such as a buffer(s), a diluent(s), a standard(s), and/or any other material useful in sample processing, washing, or conducting any other step of the assay.

Test kits according to the invention preferably include instructions for carrying out one or more of the immunoassays of the invention. Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

EXAMPLES

The following examples are offered to illustrate, but not to limit, the claimed invention.

Example 1

Periostin: Novel Tissue and Urinary Biomarker of Progressive Renal Injury Induces a Coordinated Mesenchymal Phenotype in Tubular Cells Abstract Background: Periostin acts as an adhesion molecule during bone formation. Knowledge of expression of periostin in kidney injury is still scanty.

Methods: We investigated periostin function and expression in vitro of distal nephron tubular cells (DT), in Sprague-Dawley rats after 5/6 nephrectomy (Nx), in DBA2J mice after streptozotocin-induced diabetes (SZ-DM), and in the urine of chronic kidney disease (CKD) patients.

Results: Periostin was identified by microarray and confirmed by real-time PCR in renal tissue after 5/6Nx, and SZ-DM demonstrating generalizability of the periostin increment in renal injury. Periostin was expressed predominantly in DT and in tubule cells shed into the lumen. In affected DT after 5/6Nx, periostin expression appeared de novo, the epithelial cell adhesion molecule E-cadherin became undetectable, and tubule cells displayed the mesenchymal marker proteins fibroblast specific protein-1 (FSP1) and matrix metalloproteinase-9 (MMP9). To assess whether periostin plays a direct role in renal tubular epithelial mesenchymal transition (EMT), we overexpressed periostin in cultured DT. Overexpression dramatically increased MMP9 and FSP1 protein, and decreased E-cadherin protein expression. In addition, the effect of periostin on the renal tubular EMT was also blocked by periostin siRNA transfection. Urine periostin excretion increased over time after 5/6Nx, and it was also excreted in the urine of CKD patients. Urine periostin ELISA at a cutoff value of 32.66 pg/mg creatinine demonstrated sensitivity and specificity for distinguishing patients with progressive CKD from healthy people (92.3%, and 95.0%, respectively).

Conclusions: These data demonstrate that periostin is a mediator and marker of EMT, and a promising tissue and urine biomarker for kidney injury in experimental models and in clinical renal disease.

Introduction

The aim of the present study was to investigate periostin expression and function in animal models of kidney disease and in CKD patients.

Subjects and Methods

Animals

Sprague Dawley rats (N=18) underwent 5/6nephrectomy (Nx) (N=9) by unilateral Nx and ligation of ⅔ of the vessels to the contralateral kidney or sham Nx. Rats were sacrificed at 2 days, 2 weeks, and 4 weeks after surgery. Diabetes was induced in DBA2J mice by intraperitoneal injection of streptozotocin 40 mg/kg/day for 5 days as previously described with minor modifications.[15] At 2 months, renal tissues were harvested. DBA2J mice were subjected to unilateral ureteral obstruction (UUO) of left kidney and renal tissues were harvested at 5 and 14 days. All procedures were performed in accordance with the guidelines established by the National Research Council Guide for the Care and Use of Laboratory Animals.

Gene Array Analysis

AFFYMETRIC GENE CHIP 230_2 expression analysis was used to compare the transcription profiles between normal kidneys and remnant kidney (RK) at 2 days, 2 weeks and 4 weeks after 5/6Nx. Total RNA from 3 RK at each time point and 3 normal kidneys were labeled and hybridized to AFFYMETRIC GENE CHIPs. Data were expressed as the average differences between the perfect match and mismatch probes for the periostin gene.

Collection of Human Urine

CKD subjects were recruited from our outpatient Nephrology clinic. Random urine samples were collected from proteinuric CKD patients (n=21) and non proteinuric CKD patients with PKD (n=5) and stored at −80° C. with protease inhibitors until assayed. Control samples were collected from healthy volunteers (n=20) who have normal renal function.

Quantitative Real Time-Polymerase Chain Reaction (RT-PCR) Analysis

Total RNA was isolated from rat control kidneys and RK at 2 days, 2 weeks and 4 weeks after 5/6Nx and DBA2J mice control kidneys and streptozotocin-induced diabetes (SZ-DM) at 2 months. RT-PCR with relative quantification of periostin copy number in relation to 18s ribosomal RNA transcripts was carried out using the following primers: periostin forward TGGTGTTGTCCATGTCATCGA (SEQ ID NO:1); and periostin reverse TGTGAAGTGACCGTCTCT-TCCA (SEQ ID NO:2). All PCRs were run in an ABI 7900 Sequence Detection System (Applied Biosystems).

Immunohistochemistry

Four micron sections of formalin-fixed, paraffin-embedded tissue were deparaffinized and rehydrated. Endogenous peroxidase activity was quenched by incubating the slides in endogenous enzyme block solution, and subsequently at 4° C. for overnight with the primary polyclonal periostin antibody, fibroblast specific protein-1 (FSP1) antibody and matrix metalloproteinase-9 (MMP9) antibody. Next, the sections were incubated with dextran polymer conjugated with horseradish peroxidase and affinity isolated immunoglobulin for 30 minutes at room temperature.

Immunofluorescence

Deparaffinized rat kidney sections prepared as described were double labeled with a primary rabbit polyclonal periostin antibody and either fluorescence-conjugated peanut agglutinin (PNA) lectin antibody specific for distal nephron tubules (DT), fluorescence-conjugated phaseolus vulgaris erythroagglutinin (PHA-E) lectin antibody specific for proximal nephron tubules, and/or FITC-conjugated monoclonal E-cadherin antibody. In addition, using serial sections and PNA as a marker of DT, we compared the localization of periostin and E-cadherin in the DT. Indirect primary antibody was followed with goat anti-rabbit IgG conjugated to Texas Red.

Immunoblotting Analysis

Frozen kidney tissue and cell lysates were standardized by protein concentration, and a total of 30-100 µg of protein per well was loaded. Spot urine was collected from rats, patients, and healthy volunteers. Two percent of the urinary volume for each rat sample and 0.03 ml urine for each human sample was subjected to immunoblotting analysis. The procedure was done with a standard protocol as described previously. [16]

Urine Periostin Analysis by ELISA 96-well microplates were coated overnight with 1 µg/ml (0.1 µg per well) of anti-periostin antibody. Plates were washed three times with 0.05% Tween 20 in PBS then blocked with Reagent Diluent for at least one hour. 100 µl of all standards and patient samples was added to the 96-well plate and incubated for 2 hours. After a 1 hours incubation with a rabbit polyclonal antibodies to periostin, 20 minutes incubation with dextran polymer conjugated with horseradish peroxidase, and 20 minutes incubation with substrate solution, stop solution was added to each well. Periostin absorbances were calculated by making measurements at 450 nm and correcting for plate artifact at 570 nm. Periostin concentrations were calculated based on a log-transformed standard curve.

Urine Neutrophil Gelatinase-Associated Lipocalin (NGAL) Analysis by ELISA

The urine NGAL ELISA was performed using a commercially available assay (NGAL Rapid ELISA Kit 037; Bioporto, Grusbakken, Denmark) that specifically detects urine NGAL. The assay was performed as per the manufacturer's protocol.

Generation of Periostin-Producing Mouse Distal Convoluted Tubule (MDCT) Cells and RNA Interference Full-length mouse periostin cDNA was subcloned into a pCMV-SPORT6 (Thermo Scientific, Huntsville, Ala.). All the plasmids were purified with the Qiagen Midiprep kit. One day before transfection experiment, $6 \times 10^5$ immortalized MDCT cells, kindly provided by Dr. Peter Friedman, were plated on each well of 60 mm culture dish overnight. Confluent cells (80-90%) were then transfected with the periostin construct or vector control. For knockdown of periostin expression by using RNA interference technique, cells were co-transfected with mouse periostin plasmid and SureSilencing siRNA plasmids for mouse periostin by using FuGENE HD transfection reagent, according to the manufacturer's instruction. After transfection for 24 hours, cells were lysed and protein levels were determined by immunobloting.

Statistical Analysis

Statistical analysis was performed using SPSS, version 15. Either a two-sample t test or Mann-Whitney rank sum test was used for continuous variables. For multiple comparisons, ANOVA was used followed by the least significance difference test. Spearman correlation coefficients were used as appropriate to test correlations between urine periostin and other variables. Receiver operating characteristics (ROC) analysis was used to calculate the area under the curve (AUC) for periostin and NGAL and to find the best cut-off values for identifying the CKD. A $P \leq 0.05$ was considered statistically significant.

Results

Overexpressed Periostin Gene Following Renal Injury in the RK Model

Microarray Gene Set Enrichment Analysis (GSEA, Cambridge, Mass.) showed that gene expression of periostin was significantly up-regulated in the RK inclusive of the necrotic areas: 21.91-fold at day 2, 13.32-fold at week 2, and 14.46-fold at week 4 when compared with control kidneys. To confirm the microarray observation, and to determine if it is expressed exclusively in the infarct region, we additionally examined the expression of periostin mRNA in separate RK tissues in which the infarcted region was excised. As shown in FIG. 1A, RT-PCR revealed that there was a significant difference in mRNA expression of periostin in the RK: 3.84-fold at day 2 ($P=0.025$), 9.57-fold at week 2 ($P=0.015$), and 11.05-fold at week 4 ($P=0.046$) compared with control kidneys. Thus, the examination of periostin mRNA in viable RK tissue without infarcted tissue unmasked a progressive increase seen in injured renal parenchyma after 5/6Nx.

Renal Periostin Expression Increased Over Time in the RK Model

Immunoblotting and immunohistochemical analyses were performed on RK tissue after 5/6Nx compared to control kidneys to determine periostin protein expression. FIG. 1B shows increase in renal periostin/$\beta$-actin ratio each time point after 5/6Nx compared to controls ($P<0.05$). As shown in FIG. 1C staining of kidney sections of RK at all times demonstrated periostin expression predominantly in tubular cell cytoplasm, particularly in the apical aspects, but there was no periostin present in control cortical kidney. Detached tubular cells and cytoplasmic cell fragments sloughed into tubular lumina frequently were positive for periostin. The intensity of the tubular cell staining increased between 2 days and 2 weeks after 5/6Nx and remained at 4 weeks. RK had also periostin positive interstitial cells which frequently were in the periadventitial area around arterioles. Thus, these data confirmed that the mRNA changes observed after 5/6Nx were translated into increased protein expression in tubules in the non-infarcted RK.

Overexpression of Renal Periostin in SZ-DM, and UUO

Figure 2C:
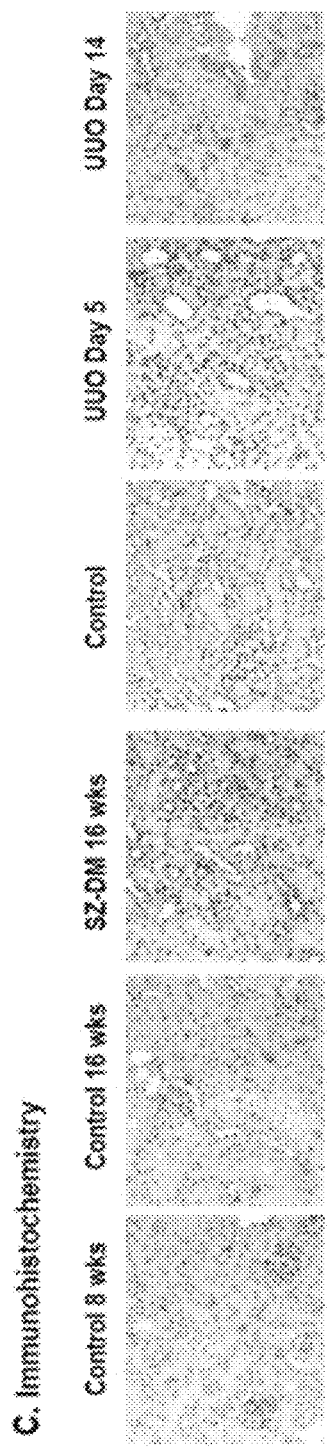
FIG. 2. Renal periostin expression increased after diabetes induction and UUO in mice. (A) Renal periostin mRNA expression increased after 2 months of SZ injection in DBA2J mice compared to control kidneys. The expression of 18 S was used as an internal control.* $P<0.05$ vs. control. (B) Renal periostin protein was increased in SZ-DM DBA2J mice compared to control DBA2J mice at 8 week and 16 weeks. * $P<0.05$ vs. DBA2J mice control kidneys 8 weeks, #$P<0.05$ vs. DBA2J mice control kidneys 16 weeks. (C) Representative micrographs showed positive periostin immunostaining in renal tubules of SZ-DM at 2 months and UUO at 5 days and 14 days. (Original magnification: 200×).

Periostin was measured by RT-PCR in renal tissue from DBA2J mice 2 months after SZ or diluent injections. FIG. 2A shows a 2.66-fold increase in periostin mRNA in the renal tissue of SZ-DM mice compared to controls ($P=0.008$). Significantly increased periostin expression was also detected by immunoblotting analysis in SZ-DM renal tissue compared with controls (FIG. 2B). As shown in FIG. 2C staining of kidney sections of SZ-DM and UUO demonstrated that prominent periostin was identified diffusely in tubular cell cytoplasm. Therefore, these data demonstrated that renal periostin also increased in a kidney injury model lacking infarction.

Periostin is Expressed in DT

As shown in FIG. 3, periostin was expressed in the cytoplasm of tubular epithelial cells that also stained positively for PNA lectin, indicating periostin expression in DT. There was no periostin identified in nephron segments stained with the proximal tubular lectin marker PHA-E. Thus periostin localized to the DT in the RK.

Figure 4A:
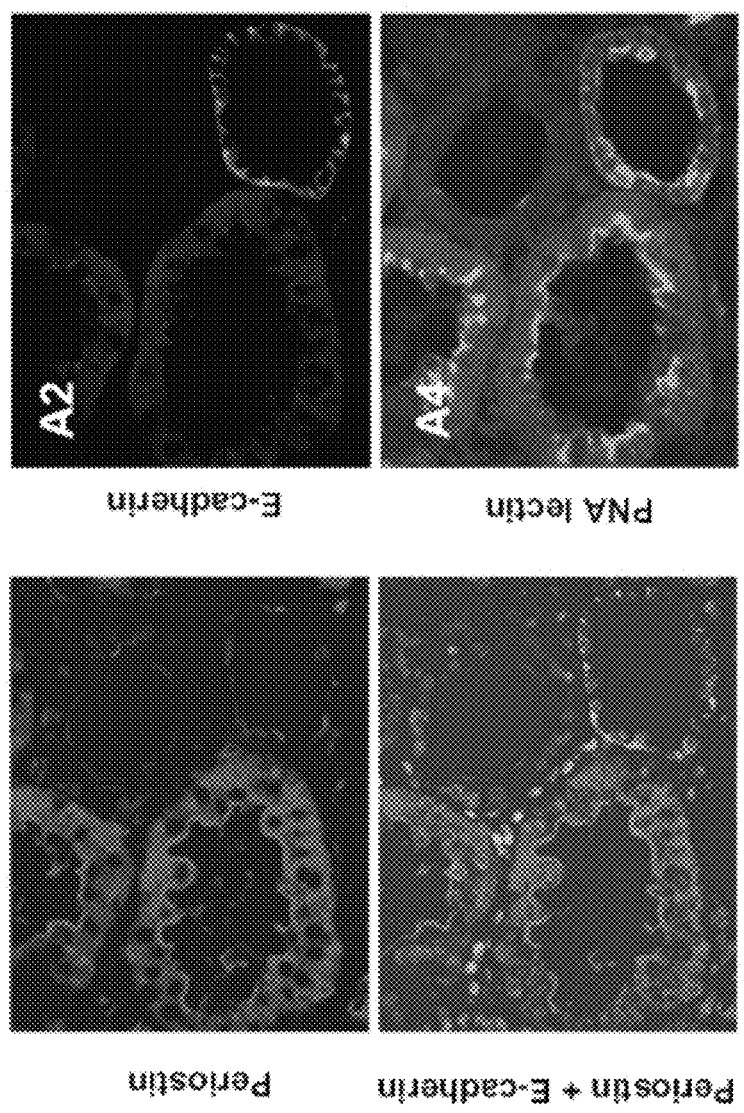
FIG. 4. Periostin induces EMT phenotype. (A) E-cadherin expression is lost in distal nephron tubules expressing cytoplasmic periostin after 5/6Nx. The serial sections show virtually mutually exclusive immunofluorescence staining patterns for cytoplasmic periostin (red, A1) and E-cadherin (green, A2) in RK tissues 4 weeks after 5/6Nx. The section was counterstained with DAPI to visualize the cell nuclei and the tubules (merge, A3). Sequential sections also show that tubules expressing either periostin or E-cadherin both continued to express PNA lectin (A4), demonstrating that both are being expressed in distal nephron tubules. (B) Periostin, FSP1, and MMP9 are co-expressed in RK 2 days, 2 weeks, and 4 weeks after 5/6Nx. Serial sections of remnant kidney were stained for Periostin (B1, B4, B7, B10), FSP1 (B2, B5, B8, B11), and MMP9 (B3, B6, B9, B12) at all time points after 5/6Nx; 2 days (B1-3); 2 weeks (B4-6); and 4 weeks (B7-12) B1-9: Staining of MMP9 and FSP1 showed co-localization with periostin in renal tubular epithelium, and in luminal sloughed tubular cells and cytoplasmic fragments at all times after 5/6Nx. Cell and luminal cellular debris stain for all three proteins at 2 weeks (arrows) (Original magnification: 600×). B10-12: Interstitial cells in the 4 week remnant kidney also stain for periostin, FSP1 and MMP9 (arrows) (Original magnification 400×).

Disappearance of the Tight Junction Protein E-Cadherin in DT Expressing Periostin Using serial sections, immunofluorescence analysis of the RK demonstrated that DT retained their affinity for PNA lectin whether the tubules did or did not express periostin. However, in these PNA lectin-positive DT, the expression of E-cadherin and periostin were virtually mutually exclusive (FIG. 4A). These studies demonstrated an association between the appearance of periostin in DT in the RK concomitant with the disappearance of the DT protein E-cadherin, the latter a marker of the tubular differentiated state and a transmembrane protein responsible for cell-cell adhesion.

Figure 4B:
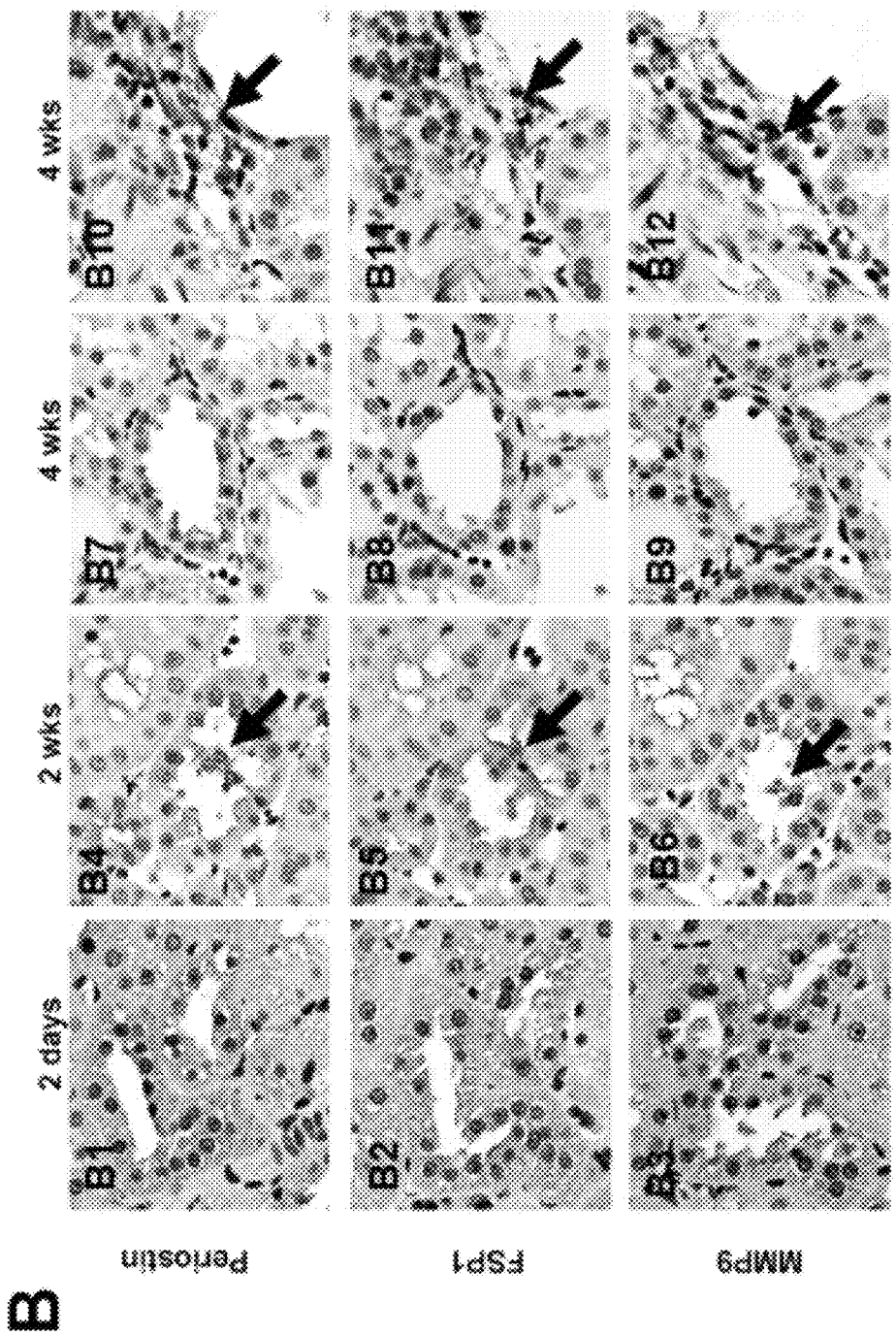

Periostin Associates with the Appearance of Renal Tubular Epithelial Mesenchymal Transition (EMT) Markers To study EMT, tissues were stained for FSP1, a cytoplasmic marker of epithelium undergoing mesenchymal transition, and MMP9, a protein involved in the turnover of extracellular matrix in renal tissue remodeling. These immunohistochemical studies revealed co-staining of MMP9 and FSP1 with periostin in affected DT cells, including sloughed cells and cytoplasmic fragments in tubular lumina, at all time points after 5/6Nx (FIG. 4B). There was staining of interstitial cells for periostin, FSP1 and MMP9 at 2 weeks with more extensive interstitial staining at 4 weeks. These studies demonstrate an association between periostin expression and the appearance of specific proteins in renal tubule indicating EMT.

In Vitro Periostin Induces Renal Tubular Mesenchymal Phenotype

Figure 5A:
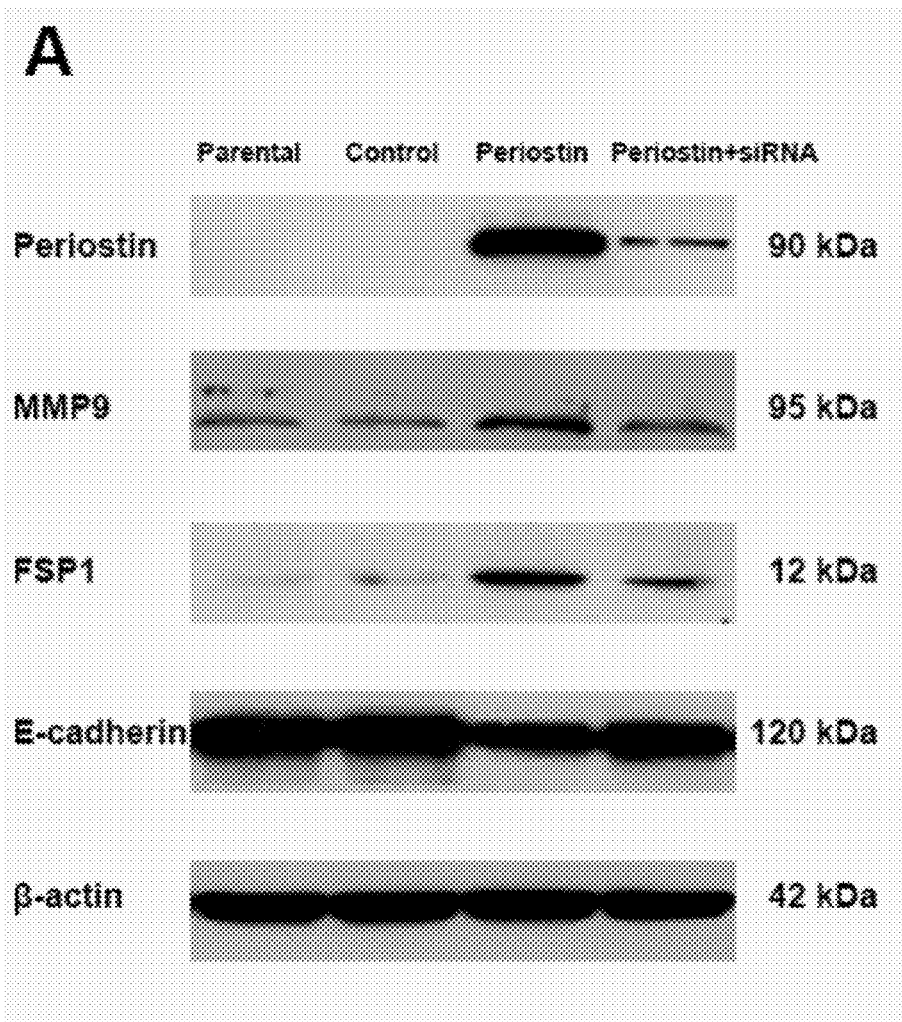
FIG. 5. Periostin-producing cells increase expression of EMT markers. Cell lysates from parental cells, transfected empty vector cells (control), transfected periostin vector cells and co-transfected periostin with SureSilencing siRNA vector cells were employed to examine MMP9, FSP1, and E-cadherin expression. MDCT cells expressing periostin dramatically increased MMP9 and FSP1 expression, a hallmark for mesenchymal cell. E-cadherin expression was also decreased by the periostin transgene in the cells. Co-transfected periostin and SureSilencing siRNA vector cells expressed reduced levels of periostin protein. Reduced periostin expression resulted in a restoration of E-cadherin and partial reduction of MMP9 and FSP1 expression. * $P<0.05$ vs. parental, control and periostin+siRNA group.
Figure 5B:
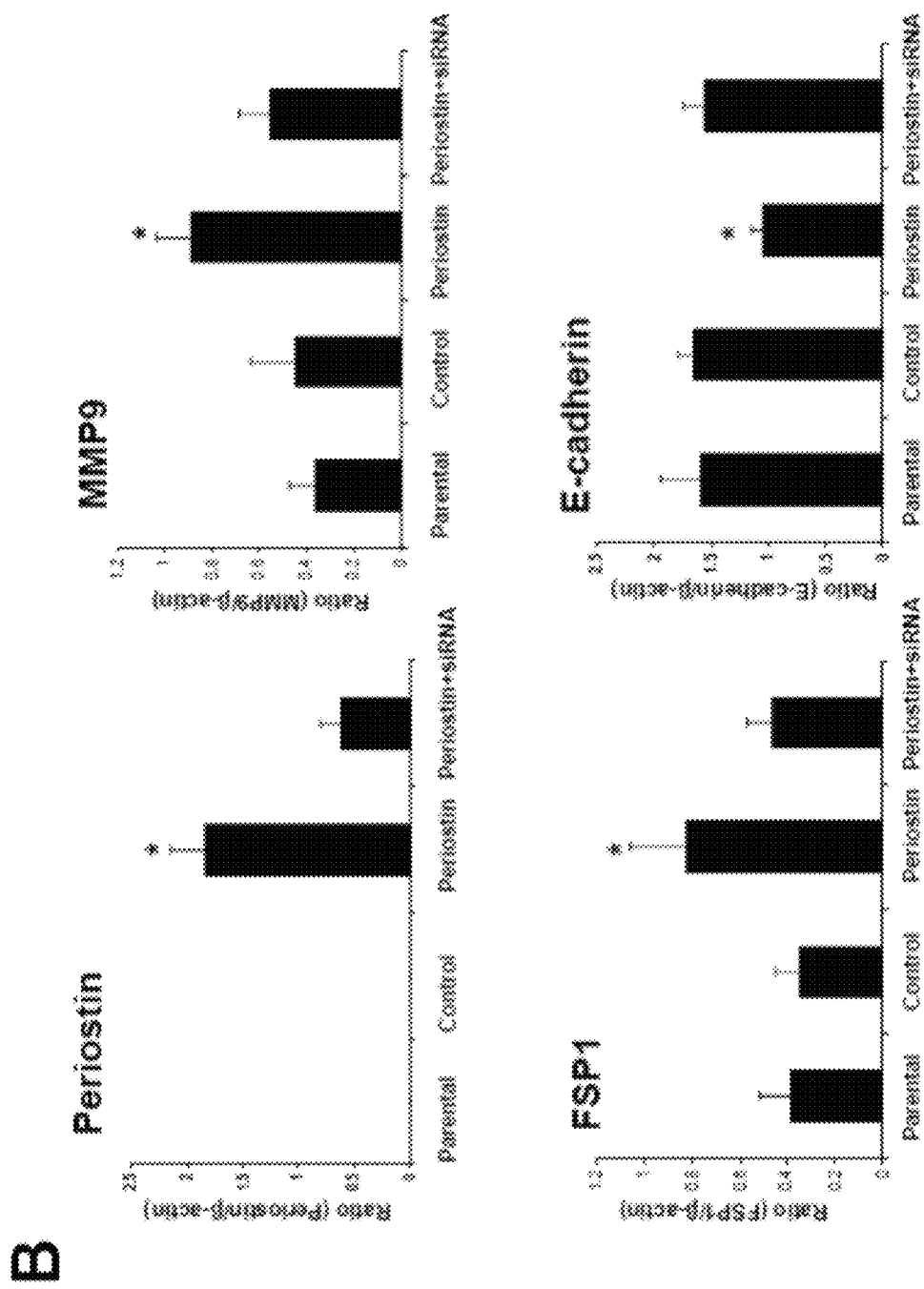

We used a transfection system to introduce the periostin cDNA into MDCT cells. MDCT cells ectopically expressing periostin dramatically increased MMP9 and FSP1 expression, a hallmark for mesenchymal cells. The level of MMP9 and FSP1 in parental MDCT cells and vector control cells was barely detectable. In contrast, expression of E-cadherin tight junction was strikingly decreased in periostin-producing cells (FIG. 5). Gene knockdown with siRNA was next applied to analyze the function of periostin on renal tubular EMT. MDCT cells were co-transfected with the periostin cDNA and siRNA, and the periostin protein level was obviously reduced. The effect of periostin on the renal tubular MMP9 and FSP1 generation and E-cadherin reduction was blocked by periostin siRNA transfection (FIG. 5). In aggregate, the data demonstrate that periostin expressed by MDCT cells drives the cells to undergo EMT.

Urinary Periostin Excretion Progressively Increased Over Time in the RK Model

Figure 6A:
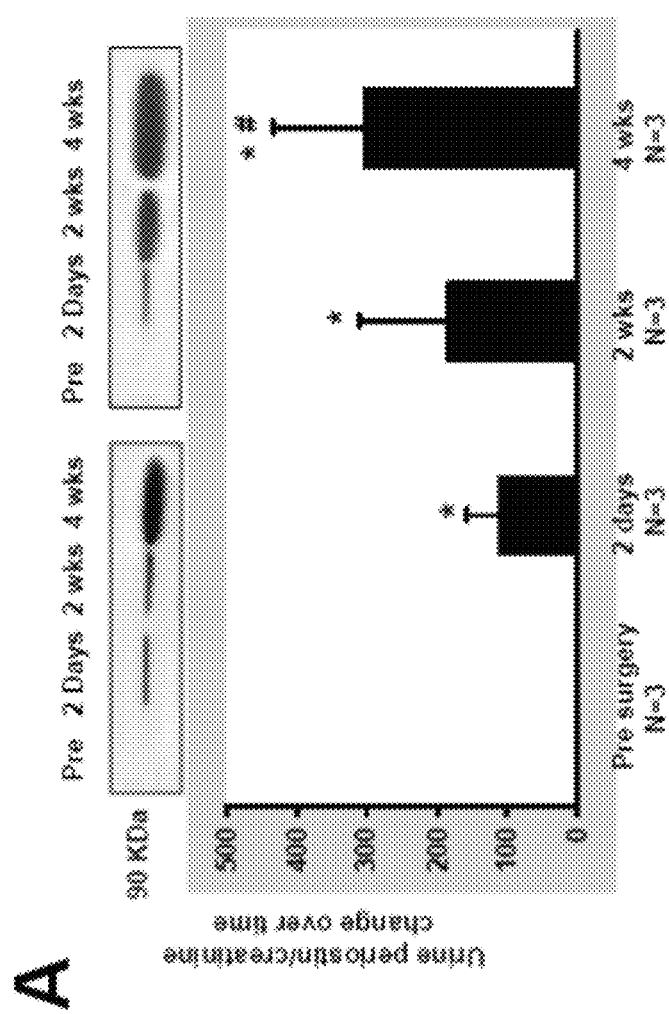
FIG. 6. Urine periostin excretion rate increase after 5/6Nx in the RK model of progressive renal injury and in patients with proteinuric renal diseases and non-proteinuric renal disease. (A) Western blotting analysis for urine periostin was performed on individual rats prior to 5/6 Nx and after 2 days, 2 weeks, and 4 weeks (n=3 at each time point). Each lane was loaded with 2% of the total urinary flow rate for each rat sample. Urine creatinine was measured and used to control for concentration. Representative Western blots are shown. Experiments were performed in triplicate. * $P<0.05$ vs. pre surgery group, # $P<0.05$ vs. 2 days after 5/6Nx group. (B) In lightly centrifuged urine treated and stored with protease inhibitors, then thawed for the assay, 90 kDa urine periostin was detectable in patients with various proteinuric glomerular diseases, but not in controls (0.03 ml urine). With urine collected identically, in patients with non-proteinuric PKD but not in controls, 90 kDa urine periostin is also clearly detectable. C, control; DN, Diabetic nephropathy; LN, Lupus nephritis; FSGS, Focal and segmental glomerulosclerosis; PKD, Polycystic kidney disease.

FIG. 6A shows the time course for the urine periostin after 5/6Nx in a longitudinal experiment in which urine was collected from the same animals serially until their sacrifice at 4 weeks. Urine periostin was undetectable during the control period prior to 5/6Nx. There were significant incremental increases in urine periostin excretion over time after 5/6Nx.

These data show that urine periostin distinguished healthy from injured kidney in a categorical fashion, and excretion increased over time with progressive chronicity of injury.

Human Urine Periostin is Detectable by Immunoblotting in CKD Patients

Figure 6B:
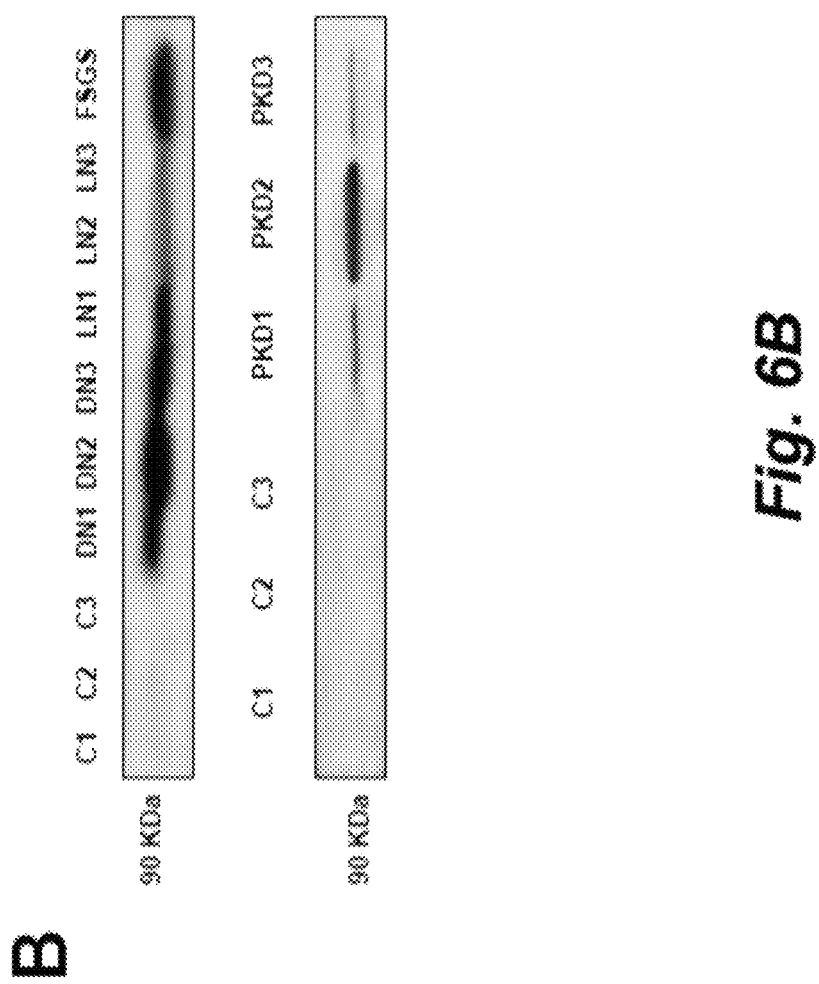

In FIGS. 6B-C, urine periostin is clearly detectable both in the proteinuric and non-proteinuric CKD patients. The appearance of urine periostin in CKD patients but not in healthy controls underscores its value as a potential biomarker for kidney injury in proteinuric and non-proteinuric conditions.

Using a Quantitative ELISA, Urine Periostin is Higher in Proteinuric and Non-Proteinuric CKD Patients than in Healthy Controls A standard curve was generated using known concentrations of recombinant periostin resulting in a linearized $R^2$ of 0.981 (data not shown). Table 1 describes the clinical characteristics of the patients.

proteinuria (R=0.30, P=0.129). These data are consistent with the hypothesis that the urine periostin measurement reflects tubular injury, and that proteinuria and urine periostin excretion are independent processes.

Urinary Periostin is High Performance in Diagnosing CKD

Figure 7A:
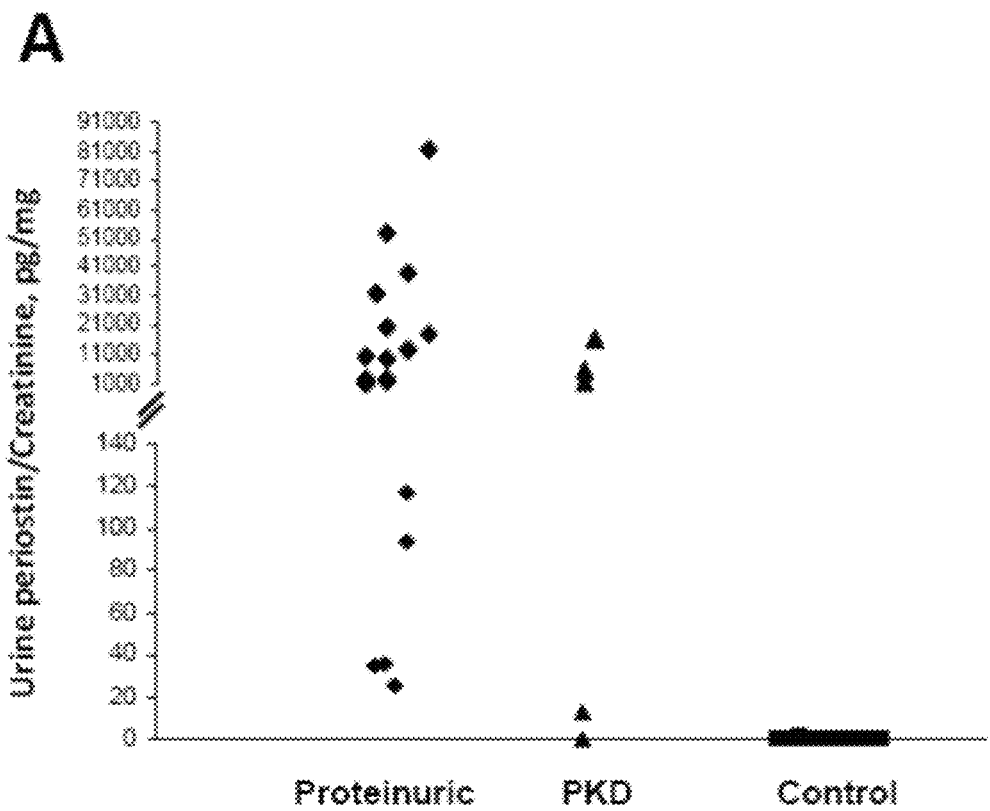
FIG. 7. Urine periostin ELISA has high performance in diagnosing CKD and it correlates with decline of GFR and increment of urine NGAL. (A) Urine periostin/creatinine measured by ELISA is higher in patients with progressive proteinuric renal disease (n=21) and in PKD (n=5) than in healthy controls (n=20). Individual values for each patient and control represents the average of at least triplicate testing. The median values for patients with progressive proteinuric disease (2473.58 pg/mg), and PKD (9504.94 pg/mg) were not significantly different from each other, but were significantly higher than for healthy controls (0 pg/mg). (B) Univariate baseline statistical correlations (Sperman coefficient) of urinary periostin. Significant correlations were evidenced with estimated GFR (B1), serum creatinine (B2), and urinary NGAL (B4). (C) Receiver operating characteristics curves of urinary periostin and NGAL considering CKD as status variable. The area under the curve for urinary periostin and NGAL was 0.96 (95% CI, 0.91 to 1.02) and 0.86 (95% CI, 0.75 to 0.97), respectively. Both urinary periostin and NGAL areas were statistically different with respect to that of diagnostic reference line ($P<0.001$). On the contrary, the difference between the two biomarker areas was non-significant ($P=0.09$).
Figure 7C:
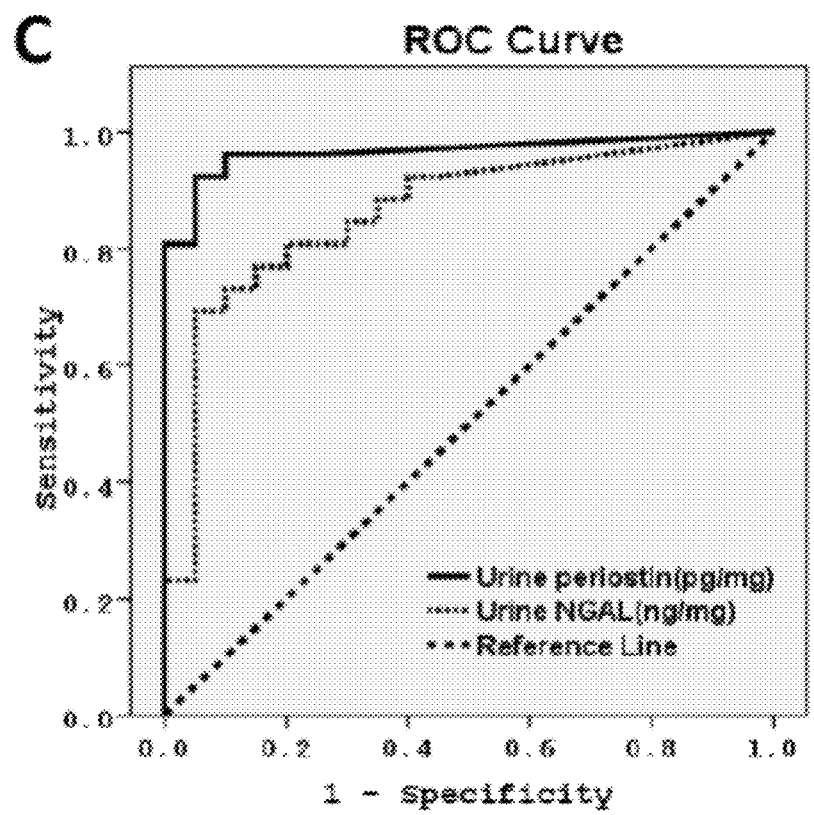

The ROC analysis of urine periostin and NGAL in diagnosing CKD is illustrated in FIG. 7C. AUC for urine periostin and NGAL were 0.96 (95% CI, 0.91 to 1.02) and 0.86 (95% CI, 0.75 to 0.97), respectively. Urine periostin and NGAL areas were statistically different with respect to that of diagnostic reference line (P<0.001), but the both biomarker areas were non-significant different (P=0.09). For urine periostin the best cut-off level was 32.66 pg/mg (sensitivity 92.3%, specificity 95.0%), whereas for urine NGAL it was 13.73 ng/mg (sensitivity 80.8%, specificity 80.0%). Thus, urine periostin ELISA demonstrate high sensitivity and specificity for diagnosing CKD and is comparable to urinary UGAL.

TABLE 1

Clinical characteristics of the patients with proteinuric and non proteinuric chronic kidney disease

| Etiology of CKD | Mean Age (yrs) | Gender | Serum Albumin (g/dL) | BUN (mg/dL) | Serum Creatinine (mg/dL) | UPCR | eGFR (mL/min/1.73 m$^2$) |
|---|---|---|---|---|---|---|---|
| Proteinuric patients (n = 21) | 46.1 ± 14.2 | F = 7, M = 14 | 3.1 ± 0.8 | 49.3 ± 26.3 | 3.1 ± 1.7 | 4.6 ± 2.8 | 35.4 ± 34.1 |
| DN (n = 13) | 52.5 ± 10.3 | F = 2, M = 11 | 3.4 ± 0.5 | 60.8 ± 19.9 | 3.7 ± 1.5 | 4.0 ± 1.9 | 20.4 ± 6.9 |
| GN (n = 8) | 35.8 ± 14.7 | F = 5, M = 3 | 2.6 ± 1.1 | 30.5 ± 25.4 | 2.2 ± 1.7 | 5.7 ± 3.8 | 59.9 ± 46.1 |
| LN (n = 2) | 20.5 ± 2.1 | F, M | 2.5 ± 0.0 | 46.0 ± 46.7 | 2.9 ± 3.1 | 4.2 ± 1.4 | 59.9 ± 62.9 |
| MN (n = 3) | 41.0 ± 14.4 | F = 2, M | 2.5 ± 1.2 | 31.6 ± 18.0 | 2.7 ± 1.4 | 7.0 ± 1.6 | 34.8 ± 31.2 |
| IgMN (n = 2) | 35.5 ± 17.7 | F = 2 | 2.6 ± 2.1 | 7.5 ± 4.9 | 0.7 ± 0.2 | 7.4 ± 7.8 | 113.4 ± 20.8 |
| FSGS (n = 1) | 51.0 | M | 3.3 | 42.0 | 2.5 | 1.6 | 28.6 |
| Non proteinuric patients (n = 5) | | | | | | | |
| PKD (n = 5) | 42.2 ± 12.8 | F = 3, M = 2 | 3.6 ± 0.3 | 39.0 ± 22.7 | 3.6 ± 2.4 | 0.4 ± 0.2 | 28.7 ± 24.8 |

BUN, Blood urea nitrogen; UPCR; Urine protein creatinine ratio, eGFR; estimated glomerular filtration rate, DN, Diabetic nephropathy; LN, Lupus nephritis; MN, membranous nephropathy, IgMN, IgM nephropathy, FSGS, Focal and segmental glomerulosclerosis; PKD, Polycystic kidney disease Urine periostin was measured by ELISA in proteinuric CKD (n=21), non proteinuric CKD (n=5), healthy controls (n=20), and in an additional two patients with non-progressive CKD (minimal change nephropathy (MCD) and Wegener's granulomatosis). The median urine periostin in healthy controls (0 pg/mg) was significantly less than in patients with proteinuric CKD (2473.58 pg/mg, p<0.001), and non-proteinuric CKD (9504.94 pg/mg, p=0.003) (FIG. 7A). There was no significant difference between the median values in the patients with proteinuric CKD and non-proteinuric CKD (p=0.72). One patient had frequently relapsing MCD, but still had 1.2 gm proteinuria/24 hours at the time the urine specimen was taken. A second patient had a history of Wegener's granulomatosis in clinical remission for over 10 years, but had 0.8 gm proteinuria/24 hours and stable serum creatinine of 2 mg/dl at the time of the urine periostin measurement. In both cases, the periostin measurements were zero.

To assess the relationship between urine periostin and renal severity, the Spearman correlation analysis was performed as appropriate. The results are illustrated in FIG. 7B. The urine periostin levels directly correlated to serum creatinine (R=0.41, P=0.03), and urine NGAL (R=0.64, P<0.001), whereas inverse significant correlations were evidenced with estimated glomerular filtration rate (GFR) (R=−0.39, P=0.04), but it did not significantly correlate with degree of Case Vignette Demonstrating the Use of Urine Periostin Measurements in Clinical Practice As a case in point, urine periostin was compared to serum creatinine in detecting kidney injury in a 20-year old woman who presented with 1 month of rapid onset malar rash, myalgias, tactile fevers, and edema. Proteinuria was 3.3 gm/day. Serum creatinine was 1.0 mg/dl (range 0.9-1.2 mg/dl) during a 1-week period. Serology confirmed systemic lupus erythematosus. Renal biopsy showed proliferative glomerulonephritis with areas of established tubular atrophy (FIG. 8A). Immunoblotting detected urine periostin in lightly centrifuged urine (FIG. 8B). Periostin immunostaining showed cytoplasmic tubular cells expression including expression in sloughed luminal cell fragments (FIG. 8C) and tubular cells with heavy diffuse cytoplasmic periostin immunostaining (FIG. 8D). In this clinical setting, urine periostin measurements better reflected the underlying tubular injury seen histopathologically better than the serum creatinine measurements.

Discussion

The present study describes the renal expression and urine excretion of periostin in experimental models of renal disease, and in the urine from a group of CKD patients. Urine periostin ELISA demonstrated high sensitivity and specificity for diagnosing CKD. DT expressing periostin expressed other traditional mesenchymal proteins such as FSP1 and MMP9, but not E-cadherin. Overexpressed periostin in cultured MDCT cells dramatically induces expression of EMT markers and reduces tight junction E-cadherin. Moreover, after periostin siRNA transfection, renal tubular EMT was disappeared. Taken together, these data demonstrate that periostin is a likely marker of EMT and a promising tissue and urine biomarker for kidney injury.

Periostin, originally identified in osteoblasts, functions as a cell adhesion molecule for preosteoblasts, and participates in osteoblast recruitment and spreading.[3-6] Periostin may contribute to renal tissue remodeling in a manner analogous to its functions in other injured tissues.[17,18] In previously published study, periostin was localized within PKD cyst epithelial cells, and was secreted into both the tubular lumina and the interstitium.[14] In our study, staining of kidney sections of all RK at all times demonstrated periostin expression in numerous DT, predominantly in the renal tubular epithelial cell cytoplasm, and in cells shed into the lumen. The intensity of the renal parenchymal staining was increased over time after 5/6Nx. Thus, the data suggest that the de novo expression of periostin during injury and its excretion in urine may be common events during progressive renal functional decline.

A major area of research in patients with CKD is the elucidation of EMT during renal fibrosis. Multiple reports have demonstrated elevated periostin levels in malignant cells that had undergone EMT and metastasized.[19-21] In addition, one study showed that overexpression of periostin in a tumorigenic epithelial cell line induced fibroblast-like transformation with increased expression of vimentin, epidermal growth factor receptor, MMP9, and evidence for increased cell migration, and adhesion, indicative of EMT.[22] In agreement with these previously reported studies conducted on neoplastic tissues, this study also demonstrates that overexpressed periostin in cultured MDCT cells dramatically induced the appearance of the mesenchymal markers MMP9 and FSP1, and the decrease of the epithelial cell marker E-cadherin. The combination of increased MMP9 turning over basement membrane and decreased E-cadherin diminishing cell-cell adhesion, likely contributes to DT cell sloughing, and indicates that renal tubular cell periostin expression is a marker of EMT. Previous studies have demonstrated that tubular cells expressing proteins that contribute to extracellular matrix turnover during EMT may migrate to the tubulointerstitium.[23] While renal epithelium cells can acquire mesenchymal markers in vitro, they do not directly contribute to interstitial myofibroblast cells in vivo.[24] Thus, the study reported herein suggests that tubular cells expressing a mesenchymal phenotype also are at risk of losing cell-cell and cell-matrix attachments and sloughing into the tubular lumen.

In conclusion, these studies demonstrate that periostin in the urine is a measure of the loss of renal tubular cells that have adopted a mesenchymal phenotype in response to diverse renal injuries across species. Its histopathologic expression patterns in the kidney in situ suggest that periostin may participate in the pathogenesis of CKD as a signaling molecule.

REFERENCES

1. Levey A S, Atkins R, Coresh J et al. Chronic kidney disease as a global public health problem: approaches and initiatives—a position statement from Kidney Disease Improving Global Outcomes. *Kidney Int* 2007; 72: 247-259.
2. Vassalotti J A, Stevens L A, Levey A S. Testing for chronic kidney disease: a position statement from the National Kidney Foundation. *Am J Kidney Dis* 2007; 50: 169-180.
3. Horiuchi K, Amizuka N, Takeshita S et al. Identification and characterization of a novel protein, periostin, with restricted expression to periosteum and periodontal ligament and increased expression by transforming growth factor beta. *J Bone Miner Res* 1999; 14: 1239-1249.
4. Takeshita S, Kikuno R, Tezuka K, Amann E. Osteoblast-specific factor 2: cloning of a putative bone adhesion protein with homology with the insect protein fasciclin I. *Biochem J* 1993; 294 (Pt 1): 271-278.
5. Lindner V, Wang Q, Conley B A, Friesel R E, Vary C P. Vascular injury induces expression of periostin: implications for vascular cell differentiation and migration. *Arterioscler Thromb Vasc Biol* 2005; 25: 77-83.
6. Li G, Oparil S, Sanders J M et al. Phosphatidylinositol-3-kinase signaling mediates vascular smooth muscle cell expression of periostin in vivo and in vitro. *Atherosclerosis* 2006; 188: 292-300.
7. Coutu D L, Wu J H, Monette A et al. Periostin, a member of a novel family of vitamin K-dependent proteins, is expressed by mesenchymal stromal cells. *J Biol Chem* 2008; 283: 17991-18001.
8. Kruzynska-Frejtag A, Wang J, Maeda M et al. Periostin is expressed within the developing teeth at the sites of epithelial-mesenchymal interaction. *Dev Dyn* 2004; 229: 857-868.
9. Rani S, Barbe M F, Barr A E, Litvin J. Periostin-like-factor and Periostin in an animal model of work-related musculoskeletal disorder. *Bone* 2009; 44: 502-512.
10. Litvin J, Blagg A, Mu A et al. Periostin and periostin-like factor in the human heart: possible therapeutic targets. *Cardiovasc Pathol* 2006; 15: 24-32.
11. Katsuragi N, Morishita R, Nakamura N et al. Periostin as a novel factor responsible for ventricular dilation. *Circulation* 2004; 110: 1806-1813.
12. Norris R A, Kern C B, Wessels A et al. Identification and detection of the periostin gene in cardiac development. *Anat Rec A Discov Mol Cell Evol Biol* 2004; 281: 1227-1233.
13. Ito T, Suzuki A, Imai E et al. Tornado extraction: a method to enrich and purify RNA from the nephrogenic zone of the neonatal rat kidney. *Kidney Int* 2002; 62: 763-769.
14. Wallace D P, Quante M T, Reif G A et al. Periostin induces proliferation of human autosomal dominant polycystic kidney cells through alphaV-integrin receptor. *Am J Physiol Renal Physiol* 2008; 295: F1463-1471.
15. Dai T, Patel-Chamberlin M, Natarajan R et al. Heat shock protein 27 overexpression mitigates cytokine-induced islet apoptosis and streptozotocin-induced diabetes. *Endocrinology* 2009; 150: 3031-3039.
16. Dai T, Natarajan R, Nast C C et al. Glucose and diabetes: effects on podocyte and glomerular p38MAPK, heat shock protein 25, and actin cytoskeleton. *Kidney Int* 2006; 69: 806-814.
17. Oku E, Kanaji T, Takata Y et al. Periostin and bone marrow fibrosis. *Int J Hematol* 2008; 88: 57-63.
18. Takayama G, Arima K, Kanaji T et al. Periostin: a novel component of subepithelial fibrosis of bronchial asthma downstream of IL-4 and IL-13 signals. *J Allergy Clin Immunol* 2006; 118: 98-104.
19. Gillan L, Matei D, Fishman D A et al. Periostin secreted by epithelial ovarian carcinoma is a ligand for alpha(V) beta(3) and alpha(V)beta(5) integrins and promotes cell motility. *Cancer Res* 2002; 62: 5358-5364.

20. Sasaki H, Sato Y, Kondo S et al. Expression of the periostin mRNA level in neuroblastoma. *J Pediatr Surg* 2002; 37: 1293-1297.
21. Ruan K, Bao S, Ouyang G. The multifaceted role of periostin in tumorigenesis. *Cell Mol Life Sci* 2009; 66: 2219-2230.
22. Yan W, Shao R. Transduction of a mesenchyme-specific gene periostin into 293T cells induces cell invasive activity through epithelial-mesenchymal transformation. *J Biol Chem* 2006; 281: 19700-19708.
23. Iwano M, Plieth D, Danoff T M et al. Evidence that fibroblasts derive from epithelium during tissue fibrosis. *J Clin Invest* 2002; 110: 341-350.
24. Humphreys B D, Lin S L, Kobayashi A et al. Fate tracing reveals the pericyte and not epithelial origin of myofibroblasts in kidney fibrosis. *Am J Pathol* 2010; 176: 85-97.

What is claimed is:

1. A method of assaying an indicator of, and treating, renal injury or renal disease, the method comprising:
   (a) assaying a urine sample from a subject for periostin as a diagnostic indicator of renal injury or renal disease; and
   (b) prescribing, initiating, or altering prophylaxis or therapy for renal injury or renal disease when the assayed periostin is at an elevated level relative to a normal level or range or relative to a level in a previous periostin assay from the same subject; or
   (c) altering prophylaxis or therapy for renal injury or renal disease in a subject undergoing such prophylaxis or therapy when the assayed periostin is at a level different than in a previous periostin assay from the same subject.

2. A method of assaying an indicator of, and treating, renal injury or renal disease, the method comprising:
   (a) assaying a urine sample from a subject for periostin as an indicator of epithelial mesenchymal transition (EMT);
   (b) prescribing, initiating, or altering prophylaxis or therapy for renal injury or renal disease when the assayed periostin is at an elevated level relative to a normal level or range or relative to a level in a previous periostin assay from the same subject; or
   (c) altering prophylaxis or therapy for renal injury or renal disease in a subject undergoing such prophylaxis or therapy when the assayed periostin is at a level different than in a previous periostin assay from the same subject.

3. The method of claim 1, wherein the urine sample comprises a human urine sample.

4. The method of claim 1, wherein the urine sample comprises centrifuged urine.

5. The method of claim 1, wherein the urine sample comprises urinary exosomes.

6. The method of claim 3, wherein the human is a human patient known to have, or suspected of having, renal injury or renal disease.

7. The method of claim 6, wherein the human patient is known to have, or is suspected of having, renal injury.

8. The method of claim 6, wherein the human patient is known to have, or is suspected of having, acute renal disease.

9. The method of claim 6, wherein the human patient is known to have, or suspected of having, chronic renal disease.

10. The method of claim 1, additionally comprising assaying for one or more additional indicators of renal injury or disease selected from the group consisting of serum creatinine, serum cystatin-C, urine protein, urine albumin, urine N-acetyl-beta-D-glucosaminidase, urine NGAL, IL-18, urine KIM1, and hematopoietic growth factor inducible neurokinin-1 (HGFIN).

11. The method of claim 1, wherein periostin is assayed by a method selected from the group consisting of an immunoassay, electrochemical detection, electrophoresis, capillary electrophoresis, high performance liquid chromatography (HPLC), thin layer chromatography (TLC), hyperdiffusion chromatography, mass spectroscopy, fluid or gel precipitin reactions, immunodiffusion, immunohistochemistry, affinity chromatography, immunoelectrophoresis, radioimmunoassay (RIA), enzyme-linked immunosorbent assays (ELISAs), immunofluorescent assays, Western blotting, and any combination thereof.

12. The method of claim 1, wherein periostin is assayed in a method wherein the periostin becomes labeled with a detectable label.

13. The method of claim 1, wherein periostin is assayed in a method wherein the periostin is transformed from a free state to a bound state by forming a complex with another assay component.

14. The method of claim 1, wherein periostin is assayed in a method wherein periostin initially present in a soluble phase becomes immobilized on a solid phase.

15. The method of claim 1, wherein periostin is assayed in a method wherein the sample is fractionated to separate periostin from at least one other sample component.

16. The method of claim 1, wherein periostin is assayed in a method wherein periostin becomes embedded in a separation medium.

17. The method of claim 1, wherein periostin is assayed in a method wherein periostin is volatilized.

18. The method of claim 1, additionally comprising recording the periostin level, and/or a diagnosis based at least in part on the periostin level, in a patient medical record for the subject.

19. The method of claim 18, wherein said recording comprises recording the periostin level in a computer-readable medium.

20. The method of claim 18, wherein said patient medical record is maintained by a laboratory, physician's office, a hospital, a health maintenance organization, an insurance company, or a personal medical record website.

21. The method of claim 1, additionally comprising recording a diagnosis, based at least in part on the periostin level, on or in a medic alert article selected from the group consisting of a card, worn article, and radiofrequency identification (RFID) tag.

22. The method of claim 1, additionally comprising informing the subject of a result of the periostin assay and/or of a diagnosis based at least in part on the periostin level.

23. The method of claim 1, wherein the periostin level determined in said assay is not elevated, and the method further comprises ordering and/or performing one or more additional periostin assays.

24. The method of claim 1, wherein the periostin level determined in said assay is elevated, and the method further comprises ordering and/or performing one or more additional assays.

25. The method of claim 24, wherein the additional assay comprises an additional periostin assay.

26. The method of claim 24, wherein the additional assay comprises an assay for an additional indicator of renal injury or disease.

27. The method of claim 1, wherein the urine sample is obtained from a subject after initiation of treatment for renal injury or renal disease.

28. The method of claim 11, wherein periostin is assayed by an immunoassay.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Mus musculus

<400> SEQUENCE: 1
tggtgttgtc catgtcatcg a                                             21

<210> SEQ ID NO 2
<211> LENGTH: 22
<212> TYPE: DNA
<213> ORGANISM: Mus musculus

<400> SEQUENCE: 2
tgtgaagtga ccgtctcttc ca                                            22
```